United States Patent
Singh et al.

(10) Patent No.: US 10,317,395 B1
(45) Date of Patent: Jun. 11, 2019

(54) EX VIVO ENGINEERED IMMUNE ORGANOIDS FOR CONTROLLED GERMINAL CENTER REACTIONS

(71) Applicant: Cornell University, Ithaca, NY (US)

(72) Inventors: Ankur Singh, Ithaca, NY (US); Alberto Purwada, Ithaca, NY (US)

(73) Assignee: Cornell University, Ithaca, NY (US)

( * ) Notice: Subject to any disclaimer, the term of this patent is extended or adjusted under 35 U.S.C. 154(b) by 33 days.

(21) Appl. No.: 15/253,078

(22) Filed: Aug. 31, 2016

Related U.S. Application Data

(60) Provisional application No. 62/212,435, filed on Aug. 31, 2015.

(51) Int. Cl.
- *C12N 15/85* (2006.01)
- *G01N 33/50* (2006.01)
- *C07K 16/00* (2006.01)

(52) U.S. Cl.
CPC ......... *G01N 33/5088* (2013.01); *C07K 16/00* (2013.01); *G01N 2333/47* (2013.01)

(58) Field of Classification Search
None
See application file for complete search history.

(56) References Cited

U.S. PATENT DOCUMENTS

| | | | |
|---|---|---|---|
| 8,003,387 B2 * | 8/2011 | Sukumar | C07K 16/44 435/373 |
| 2002/0168757 A1 | 11/2002 | Kirk et al. | |
| 2003/0040113 A1 | 2/2003 | Mizuno et al. | |
| 2007/0065827 A1 | 3/2007 | Pauloski et al. | |
| 2009/0208918 A1 | 8/2009 | Kraft | |
| 2010/0305058 A1 | 12/2010 | Lancaster et al. | |
| 2011/0244502 A1 | 10/2011 | Ince et al. | |
| 2013/0045535 A1 | 2/2013 | Soen et al. | |
| 2013/0145486 A1 | 6/2013 | Akagi et al. | |
| 2014/0186414 A1 | 7/2014 | Ingber et al. | |
| 2014/0274953 A1 | 9/2014 | Lee et al. | |
| 2015/0252328 A1 | 9/2015 | Woodruff et al. | |
| 2016/0144068 A1 * | 5/2016 | Gaharwar | A61K 9/0019 424/423 |

FOREIGN PATENT DOCUMENTS

| | | | |
|---|---|---|---|
| WO | WO2006024489 | * | 3/2006 |
| WO | 2009/124997 A1 | | 10/2009 |

OTHER PUBLICATIONS

Ferrarini, M., et al., Ex-Vivo Dynamic 3-D Culture of Human Tissues in the RCCSTM Bioreactor Allows the Study o Multiple Myeloma Biology and Response to Therapy, PLOS One, Aug. 1, 2013, vol. 8, No. 8, e71613, 10 pages.

Kirshner, J., et al., A unique three-dimensional model for evaluating the impact of therapy on multiple myeloma, Blood, Oct. 1, 2008, vol. 112, No. 7, pp. 2935-2945.

Zhang, W., et al., Patient-Specific 3D Microfluidic Tissue Model for Multiple Myeloma, Tissue Engineering: Part C, 2014, vol. 20, No. 8, pp. 663-670.

Zdzivinska, B., et al., A comparison of cytokine production in 2-dimensional and 3-dimensional cultures of bone marrow stromal cellsof muliple myeloma patients in response to RPMI8226 myeloma cells, Folia Histochemica et Cytobiologica, 2009, vol. 47, No. 1, pp. 69-74.

Afrimzon, E., et al., Hydrogel microstructure live-cell array for multiplexed analyses of cancer stem cells, tumor heterogeneity and differential drug response at single-element resolution, Lab Chip, 2016, vol. 6, pp. 1047-1062.

Liu, J., et al., Spheroid body-forming cells in the human gastric cancer cell line MKN-45 possess cancer stem cell properties, International Journal of Oncology, Feb. 1, 2013, vol. 42, No. 2, pp. 453-459.

Calimeri, T., et al., A unique three-dimensional SCID-polymeric scaffold (SCID-synth-hu) model for in vivo expansion of human primary multiple myeloma cells, Leukemia, Jan. 14, 2011, vol. 25, pp. 707-711.

* cited by examiner

*Primary Examiner* — Michail A Belyavskyi
(74) *Attorney, Agent, or Firm* — Hodgson Russ LLP

(57) ABSTRACT

Provided are compositions and methods that relate ex vivo organoids that contain B cells and stromal cells in a three dimensional material includes a hydrogel. The hydrogel can be formed without exposure to ultraviolet light from an electronic ultraviolet light source. The hydrogel contains silicate nanoparticles (SiNPs) that are ionically bonded to a polyampholytic gelatin. The three dimensional material can be held at a temperature of at least 37 degrees Celsius and does not liquefy. The organoids exhibit mechanical properties that are similar to certain lymphoid tissues, and can include a germinal center. Methods of making the organoids are included, as are high throughput screening approaches that use the organoids for screening a variety of test agents. The organoids can synthesize a variety of compounds that can be recovered from the organoids or the organoid culture medium.

4 Claims, 23 Drawing Sheets
(20 of 23 Drawing Sheet(s) Filed in Color)

Figure 15
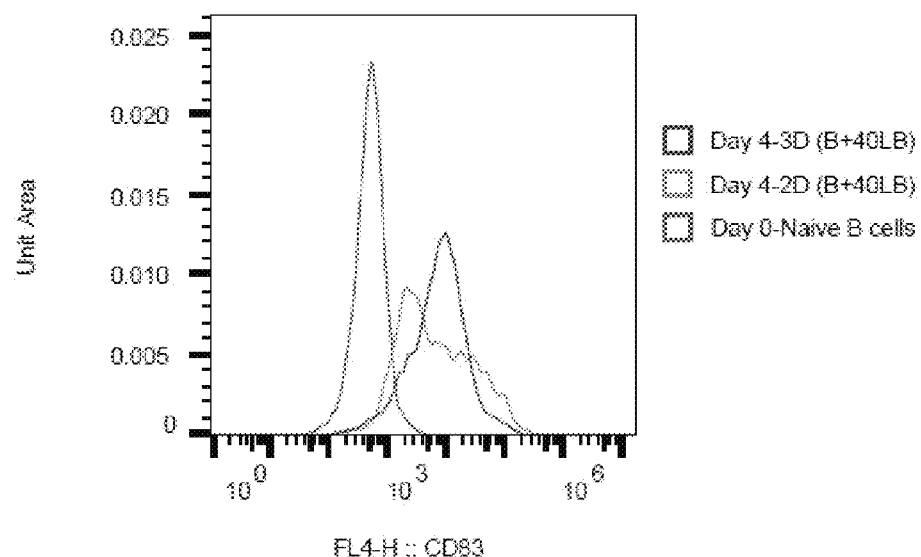
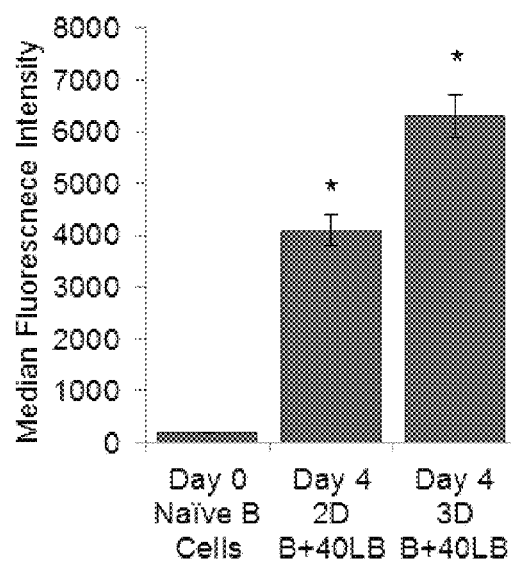

EX VIVO ENGINEERED IMMUNE ORGANOIDS FOR CONTROLLED GERMINAL CENTER REACTIONS

CROSS REFERENCE TO RELATED APPLICATIONS

This application claims priority to U.S. Provisional Application No. 62/212,435, filed on Aug. 31, 2015, the disclosure of which is hereby incorporated by reference.

STATEMENT REGARDING FEDERALLY SPONSORED RESEARCH

This invention was made with government support under 1R21CA185236-01 awarded by the National Institutes of Health. The government has certain rights in the invention.

FIELD

The present disclosure relates generally to compositions and methods that pertain to modeling and using lymphoid tissue in the form of ex vivo organoids.

BACKGROUND

Secondary immune organs, such as lymph node, tonsil and spleen, are highly structured tissues which dynamically change mechanical and biological functionality in response to antigens. Of particular importance is the activation of naïve B cells in these lymphoid tissues to form sub-anatomical structures, germinal center (GC), that program B cell conversion into antibody producing cells, which represents a powerful defense mechanism against pathogens and is characterized by immunological memory. To date, we have relied heavily on live animal models to understand immune cell development, functioning, and screening of immunotherapies against diseases, but such approaches are costly with long turnaround times. We are yet to fully understand how the cell microenvironment in lymphoid organs facilitates the GC reaction that leads to the production of antibodies. Therefore, ex vivo engineered B cell organoids could offer a new approach for studying GC B cell physiology and pathology, and potentially hematological malignancies of B cell origin, as well as screening of therapeutics including immunotherapeutics.

From an anatomical perspective, secondary lymphoid organs are composed of supporting cellular compartments, including B cell and T cells, that work together to orchestrate adaptive immune responses. B cell follicles are composed of a dense stromal network of B cell activating follicular dendritic cells (FDCs) and Arg-Gly-Asp (RGD)-presenting ECM. Activation process requires interactions between antigen-primed B cells and follicular helper T ($T_{FH}$) cells via a CD40L ligand, and secretion of IL-4. GC B cells are naturally prone to apoptosis unless rescued by anti-apoptotic signals. Although activation of B cells can be achieved through stimulation with antibodies (anti-Ig or anti-CD40), CD40L, lipopolysaccharide and cytokines, such as IL-4, in vitro, the resulting cell growth is transient with poor cell survival and previous efforts did not investigate the GC reaction in the context of lymphoid tissue microenvironment, and have not shown the ability to modulate the extent of GC reaction. Combinations of 3D scaffolds and engineered stromal cell lines for generating artificial secondary lymphoid organs have also been made, however these scaffolds have shown GC formation only when implanted in vivo by exploiting the host microenvironment. Thus, there is an ongoing and unmet need for alternative secondary immune organs that can be created and used in an ex vivo context.

SUMMARY

This disclosure pertains in part to ex vivo engineered three-dimensional organotypic cultures which permit the real-time study and control of biological functioning of mammalian tissues. In particular, the present disclosure provides in certain aspects B cell follicle organoids comprising nanocomposite biomaterials, and methods of making and using such organoids. The organoids recapitulate the anatomical microenvironment of a lymphoid tissue that provides the basis to induce an accelerated germinal center (GC) reaction by continuously providing extracellular matrix (ECM) and cell-cell signals to naïve B cells. Thus, in certain aspects the disclosure provides compositions and methods for initiating an immune reaction for antibody production at a controlled rate by providing over a sustained period survival signals to B cells that are resident within the three-dimensional organoid.

In one non-limiting demonstration the disclosure provides an RGD-presenting hydrogel scaffold reinforced with silicate nanoparticles (SiNP) as an immune organoid that contains primary naïve B cells co-cultured with stromal cells that simultaneously present $T_{FH}$ specific CD40L and B cell activating factor (BAFF), and supplemented the culture with IL-4. We show that combinations of 3D ECM structural properties, adhesive ligands, and stromal networks with signaling molecules leads to faster development and differentiation of primary naïve B cells into GC phenotype and allow control over the magnitude and rate of GC reaction. Secondary follicle organoids of this disclosure are thus suitable for recapitulating the functional aspects of lymphoid tissue to induce accelerated GC reaction ex vivo with maintained long-term cell survival by simply adjusting the extracellular signal. This approach is distinct from conventional GC induction protocols that rely on either culturing B cells as a 2D monolayer on tissue culture dishes in the presence of key molecules or transplantation of cell-seeded scaffold into live animal models for organoid formation in vivo.

DESCRIPTION OF THE FIGURES

This patent or application file contains at least one drawing executed in color. Copies of this patent or patent application publication with color drawing(s) will be provided by the Office upon request and payment of the necessary fee.

FIG. 15. Ex vivo induction into CD83 phenotype within the immune organoid. Naïve B cells with 40LB cells co-encapsulated with the immune organoids. Left panel shows the histogram overlay of flow cytometry analysis indicating a shift in CD84 signal. Right panel indicates Meadian fluorescence instensity of CD19+CD83+ cells inside the organoids and compartive controls (*p<0.01, ANOVA, n=3).

DESCRIPTION

Figure 1:
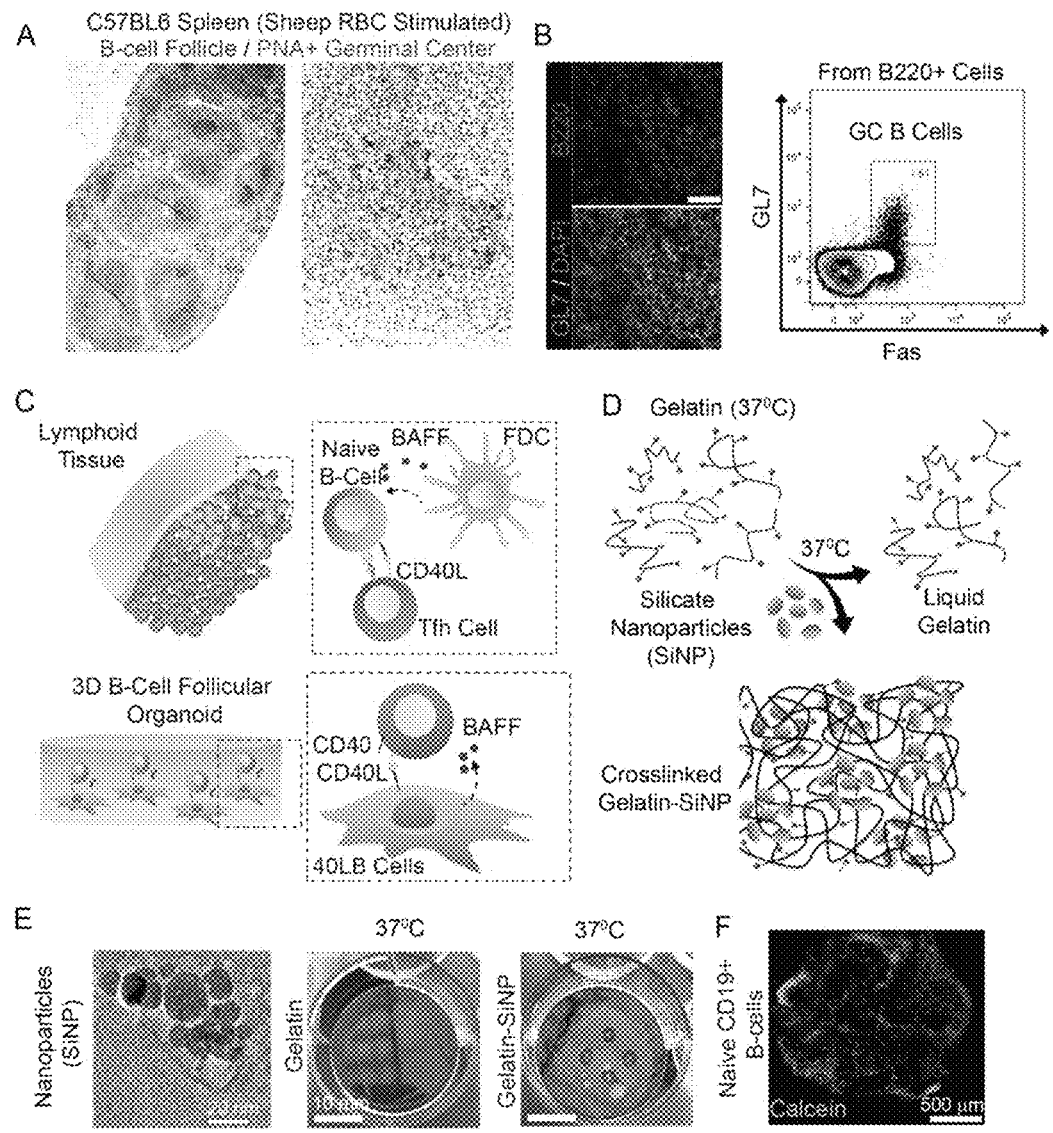
FIG. 1. Ex vivo engineered B cell follicle organoid. (A) Immunohistochemical analysis of a spleen stained for H&E and GC marker peanut agglutinin (PNA). Right panel represents immunofluorescence images of splenic tissue stained with GC marker GL7; scale bar 50 µm. (B) Flow cytometry analysis of B220+ primary B cells from immunized C57BL6 mice with the gate indicating GL7+Fas+ GC B cell population. (C) Schematic of the in vivo interaction between mature naïve B cells with follicular T helper ($T_{FH}$) cells and follicular dendritic cells (FDCs) within the lymphoid tissue follicle. FDCs produce B cell activation factor (BAFF) that support naïve B cell activation and conversion to germinal center phenotype. (D) Overview on the use of silicate nanoparticles (SiNP) for ionic crosslinking of gelatin to form stable hydrogel at 37° C. (E) TEM of silicate nanoparticles (Left, scale bar 20 nm). Hydrogels composed of gelatin only and those ionically cross-linked with SiNP were compared for gelation at 37° C. (Right, scale bar 10 mm). (F) Primary B cell viability and distribution 24 hour following the encapsulation procedure (Bottom; green: Calcein; scale bar 500 µm).

Unless defined otherwise herein, all technical and scientific terms used herein have the same meaning as commonly understood by one of ordinary skill in the art to which this disclosure pertains.

Unless specified to the contrary, it is intended that every maximum numerical limitation given throughout this description includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The disclosure generally pertains to ex vivo 3D organotypic cultures that mimic B cell follicles in the form of engineered organoids, and methods of making and using such organoids. The organoids replicate features of lymphoid tissue an accordingly provide an artificial GC that can be maintained for periods of time in culture.

The organoids generally comprise certain cell types that include but are not necessarily limited to stromal cells and B cells. In certain aspects the cells in the organoid can consist of stromal cells and B cells.

In certain aspects the stromal cells present in the organoids of this disclosure comprise modified fibroblasts, a non-limiting example of which includes 40LB stromal cells, which are known in the art express the CD40-ligand (CD40L) and B cell activating factor (BAFF). In embodiments, fibroblasts or other suitable cells may be transfected or otherwise modified such that they express a CD40L gene, and so that they express B cell activating factor (BAFF). Compositions and methods for making such modifications are known in the art. In certain embodiments, an organoid of this disclosure comprises between 20,000 to 40,000 LB stromal cells. In one example the organoid comprises at least 40,000 40LB stromal cells. In certain approaches including at least 40,000 stromal cells facilitates network formation. In certain embodiments, an organoid of this disclosure comprises at least 20,000 B cells. In certain and non-limiting examples the organoids have a volume of from 1-50 ml, and in specific examples can be in the form of droplets. In one non-limiting example the organoid is an approximately 10 μL droplet, however can be made with smaller or larger volume too. In certain embodiments stromal cells and/or B cells are encapsulated by a hydrogel that is described herein.

In certain embodiments an organoid of this disclosure exhibits certain characteristics relative to a suitable control, examples of which will be apparent to those skilled in the art when given the benefit of this disclosure. In an embodiment a suitable control comprises a 2D culture that includes, for example, the same or similar cell types as the organoid but lacks the 3D architecture of the organoid. In one embodiment, the organoids of this disclosure exhibit an increase in at least one GC specific marker relative to a control. In certain examples, the organoid exhibits from at least a 10-100 fold increase, including all integers and ranges of integers there between, in the GC-specific marker GL7. In certain embodiments the organoids exhibit at least a 10-100 fold increase, including all integers and ranges of integers there between, in CD19+ cell numbers, and/or CD19+/GL7+ cell numbers. Increases in these markers and cell types can be determined using well known approaches, given the benefit of this disclosure. Increases in cell numbers can occur and be detected over any suitable period of time during which the organoid(s) is present in an appropriate culture medium, such periods comprising from 12 hours to 10 days. In certain embodiments organoids of this disclosure comprise B cells that exhibit immunoglobulin class switching, such as from initially producing IgM, and subsequently switching to a different Ig class, such as IgG, or other Ig classes. Such class switching can be detected, for example, after an initial period in a suitable cell culture of between about 6-8 days. In certain embodiments, B cells that are comprised by an organoid of this disclosure express CD83, and the expression of CD83 can change over time and/or after exposure to, for example, a test agent and/or a known B-cell activating agent. In certain embodiments, organoids of this disclosure comprise B cells that express more CD83 than a control, such as B cells in a control 2D culture. In certain embodiments, a 3D organoid of the present disclosure comprises more viable cells over a period of time, such as 4 days, in comparison to control 2D systems when B cells were co-cultured with 40LB in media supplemented with 100 ng/mL IL-4.

Methods of the disclosure comprise testing test agents using organoids that are described herein. In certain aspects test agents are analyzed using the organoids to determine whether they exhibit an activity, such as stimulating an effect in the B cells. In embodiments methods of testing test agents comprise providing a plurality of distinct samples each comprising at least one ex vivo organoid made according to this disclosure, and/or having organoid characteristics as described herein. The plurality of samples may be configured so as to be amenable for high throughput screening. In certain embodiments, the samples are divided into a plurality of reaction chambers, such as wells in a plate or areas on a dish, and/or are configured in an array. Conventional multi-well plate, dish, tissue culture plate, or glass coverslips can be used, if silanized. Alternatively, non-treated multi-well plates can be used. In certain approaches, one or more 96-well plates are used. In embodiments, one or more 384-wells plates are used. In embodiments the effect of a test agent on ex vivo organoid as described herein can be compared to a reference. Any suitable control can be used as a reference, including but not limited to one or more organoids to which a test agent has not been added, or to which an agent with a known effect on the one or more organoids is added, or the reference can be a standardized reference, such as a known value established from previous experiments or other observations, an area under a curve, a titration, dilution, etc. The disclosure includes the testing plates that contain the organoids, and accordingly comprise in certain embodiments organoids that are in a complex with a substrate, wherein the complex can be a non-covalent or covalent connection between a portion of the organoid and the substrate. Thus the organoids can be reversibly or irreversibly attached to the substrate.

Agents can be tested for various activities (or the lack thereof) which include but are not limited to immunomodulatory functions, activating B cells, inhibiting the activation of B cells, inducing or inhibiting proliferation of B cells, formation of B plasma cells, inducing or inhibiting antibody production, stimulating or inhibiting Ig class switching, extending B cell viability in culture and/or storage, cytotoxic effects against B cells, and anti-cancer effects. Activities also include the capability to modify a phenotype a B cell or a combination of B cells and stromal cells. The test agents can accordingly be tested to identify candidates for use as pharmaceutical agents for human and veterinary purposes. In certain embodiments the test agents are tested to determine whether they are candidates for use in prophylaxis and/or therapies for a variety of disorders, including but not necessarily limited to B-cell mediated diseases such as cancers, including but not limited to lymphomas, such as Hodgkin's lymphoma (NHL) and Hodgkin's lymphoma (HL), Burkitt's lymphoma or diffuse large B-cell lymphoma, and others. The test agents can be tested to determine whether they are candidates for use in prophylaxis and/or therapies for a variety of autoimmune disorders, including but not limited to those disorders that are characterized at least in part by a loss of B-cell tolerance and/or inappropriate production of autoantibodies. In embodiments the test agents can be analyzed to determine if they can affect B cell secretion of cytokines and/or chemokines, including but not limited to proinflammatory cytokines and chemokines, such as TNF-α, IFN-γ, IL-6, and macrophage migration inhibitory factor (MIF). In embodiments the test agents can be tested to determine whether they are candidates for use in conjunction with medical immunosuppression, such as in the context of organ or other tissue transplantation, and thus may be of benefit in the area of graft-versus-host diseases. In embodiments the test agents can be tested to determine whether they are candidates for use in T-cell mediated immune responses, such as by analyzing the agents for capability to modulate the antigen-presenting function of B cells. In embodiments, the test agents can be tested to determine whether they are candidates for use in increasing or decreasing the amount of, or modulating the activity, of one or more proteins expressed by B cells, such as CD20, CD22, CD19, CD40 and CD40 ligand (CD154).

Detecting activity of a test agent can be performed using any suitable techniques. In certain embodiments, detecting activity comprises determining a change in secretion of a compound from B cells and/or stromal cells. In non-limiting embodiments the secreted compound can comprise, for example, a chemokine, a cytokine, an interleukin, or a growth factor, which can all be detecting using techniques known to the art, such as immunological detection approaches. In one embodiment, detecting activity comprises determining a change in gene expression in the B cells, which likewise can be detected using techniques known to the skilled artisan, such as by polynucleotide amplification, and/or sequencing, and immunological detection of protein expression. The determining the activity of the test agent can be qualitative or quantitative.

In certain embodiments the disclosure comprises contacting an organoid of this disclosure with an antigen. The type and composition of the antigen is not particularly limited. In embodiments the antigen is peptide, polypeptide or protein antigen. The antigen can be derived from any source of interest, including but not limited to pathogenic agents, antigens that are differentially or exclusively expressed by cells of interest, such as cancer cells, or autoimmune antigens. The organoids can also be contacted with cell or tissue lysates that may contain one or more antigens of interest, or the lysates may contain or may be suspected to contain unknown antigens that may be of interest.

Figure 16:
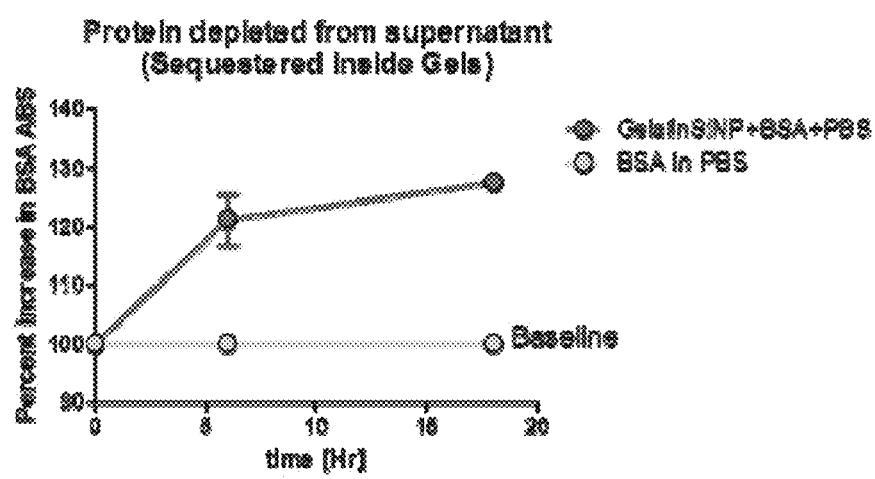
FIG. 16. Graphical depiction of datea demonstrating protein (BSA) depletion by sequestration in hydrogels, thus trapping and concentrating the protein within the hydrogel.

In certain embodiments organoids of this disclosure can be used to deplete one or more compounds from, for example, a medium in which the organoid is kept. In non-limiting examples, the organoids accordingly sequester one or more proteins within the organoid, and thus can increase the local concentration of the protein within the 3D architecture of the organoid. It will be recognized that because of this characteristic the amount and frequency of cell culture components, extracellular matrix (ECM) ligands, growth factors, cytokines, chemokines, and the like, can be altered to take into account the ability to deplete medium components in a way that is distinct from 2D cultures. A non-limiting demonstration of this effect is presented in FIG. 16, which demonstrates depletion of a representative protein (BSA) from supernatant. In embodiments, the disclosure accordingly comprises one or more organoids is media, wherein the organoids have concentrated one or more media components. In this regard, and without intending to be constrained by any particular theory, it is considered that such sequestering components of media can enhance differentiation of cells.

B cells that are included in the organoids of this disclosure can be obtained and/or expanded from human or non-human subjects. In embodiments, the B cells are naïve B cells, primary B cells, or combinations thereof. In certain examples primary B cells are freshly isolated B cells, such as from blood from an individual, and can be naïve (CD19+) or activated (GL7+ or CD138+).

The cells can be obtained from an individual of any age or gender. In certain approaches the B cells and/or stromal cells may be obtained from an individual who has been diagnosed with, is suspected of having, or is at risk for developing a disorder that is correlated with the presence of abnormal B cells.

In one aspect the disclosure encompasses isolating B cells from an individual and using the B cells directly, or processing the B cells as described herein, to form an organoid of this disclosure. Such organoids can be used in, for example, personalized medicine approaches whereby the individual's B cells as a component of the organoid can be analyzed for sensitivity or resistance to any of a variety of pharmaceutical and/or other medical interventions, or for other characteristics to determine a medical intervention or recommend a treatment or other procedure for the individual.

In certain aspects a plurality of B cells can be analyzed for use in creating organoids of this disclosure. The B cells can be screened for any characteristic of interest, such as expressing antibodies that are specific for a particular immunogen, or are susceptible to developing a particular phenotype, such as a malignant phenotype, or any other selectable characteristic. Once B cells are selected based on any user-generated selection criteria they can be incorporated into organoids according to methods of this disclosure.

In an aspect the disclosure includes a method comprising modulating an organoid of this disclosure to produce lymphoma cells. This aspect can include separating the lymphoma cells from the organoid, and optionally obtaining an isolated population of the lymphoma cells. The lymphoma cells can be used in conjunction with testing one or more test agents as described above to determine, for example, if the test agent can inhibit the growth of the lymphoma cells.

In certain embodiments organoids of this disclosure are selected based on production of a particular agent or product. In embodiments, the organoids are selected based on production of one or more cytokines, chemokines, growth factors, antibodies, ECM ligands, or combinations thereof. In embodiments the disclosure includes allowing organoids to produce one or more agents for a period of time, and then separating the agents from the organoids and/or the media in which the organoids are cultured. In embodiments the disclosure includes the cell media that contains agents secreted or otherwise produced by the organoids, including but not limited to such media from which the organoids are separated after producing the agents. The agents can be themselves separated from the organoids and/or the media and purified to any desired degree of purity using known approaches to, for example, protein purification. In one aspect B cells in the organoid produces antibodies which are subsequently separated from the B cells, and/or from the culture media. In embodiments, the B cells are converted to plasma cells and secrete antibodies. In embodiments antibodies separated from organoids and/or media described herein are homogenous for a specific epitope on an immunogen. In other embodiments a mixture of antibodies with distinct specificities may be obtained. Thus, in embodiments disclosure provides for initiating an immune reaction for antibody production at a controlled rate by providing over a sustained period survival signals to B cells that are resident within the three-dimensional organoid.

The disclosure includes mixtures or organoids that have clonal populations of B cells, or have heterogeneous B cell populations as defined by, for example, antibody specificity. The disclosure also includes mixtures of distinct organoids. In embodiments the disclosure comprises organoids that have been maintained in culture for at least 5, 6, 7, 8, 9, 10, or more days.

In certain approaches the B cells and/or stromal cells are not infected with Epstein Barr Virus (EBV). In certain embodiments, the organoids are created and/or maintained in a cell culture container, such as a dish, which is coated with a hydrophobic coating, such as a siliconizing reagent, one non-limiting example of which comprises the hydrophobic coating sold under the trade name SIGMACOTE.

In certain embodiments the SiNPs are commercially available SiNPs, such as those sold under the trade name LAPONITE.

In certain embodiments the organoids and/or the cell culture medium comprises Arg-Gly-Asp (RGD), wherein the RGD may optionally be present in an extracellular matrix.

In certain embodiment, the cell culture medium in which the organoids are cultured comprises a serum-supplemented cell culture medium. In certain implementations the culture medium contains IL-4.

In certain approaches the hydrogel comprising the SiNPs is formed without exposure to ultraviolet light from an electronic ultraviolet light source (as opposed to ultraviolet light that may be present in ambient light, or produced by an electronic light source that is not specifically designed to function as an ultraviolet light source). In an embodiment the hydrogel does not contain and is not made using any methacrylate.

The hydrogel comprises a gelatin, which can be any suitable gelatin. In embodiments, the gelatin comprises a polyampholytic gelatin that ionically interacts with anisotropically distributed opposite charges on synthetic SiNPs. The polyampholytic gelatin comprises has a mixed anion and cation character. In embodiments, the disclosure includes making and using hydrogels that remain stable and do not liquefy at 37° C. A non-limiting overview depicting the use of SiNPs via ionic crosslinking of gelatin to form stable hydrogel at 37° C. is provided in FIG. 1.

In embodiments the hydrogel comprises about 2-4% of the polyampholytic gelatin, and/or about 0.5%-2.5% of the SiNPs. In certain aspects the disclosure excludes gelatin: SiNP ratio of 2:1 and 4:1.5.

In an embodiment an organoid of this disclosure comprises a hydrogel comprising SiNPs, wherein the organoid is at a temperature of about 37 degrees Celsius and hydrogel is not liquefied. In certain embodiments the hydrogel used to create an organoid of this disclosure exhibits certain characteristic storage and/or loss modulus under physiological conditions (pH 7.4 and 37° C.). In an embodiment a storage modulus is considered a measure of stiffness. In certain embodiments hydrogels of this disclosure exhibit a stiffness of more than 130±40 Pa. In embodiments the hydrogel exhibits a stiffness that is more than 130±40 Pa, but is less than 3100±410 Pa. In embodiments, the hydrogel exhibits a stiffness that is 1900±100 Pa. In embodiments, stromal 40LB cells demonstrate enhanced spreading and network formation when cultured in matrices with ~2000 Pa storage modulus as a function of stromal cell density.

In certain embodiments, organoids of this disclosure exhibit faster differentiation of naïve primary B cells to the GC phenotype relative to a control. In certain examples the control is a 2D co-culture of fibroblasts and B cells. In certain examples organoids of this disclosure exhibit from 10-100 fold more rapid differentiation of primary naïve B cells into GC phenotype relative to a control. In embodiments, the rate of differentiation of primary naïve B cells into GC phenotype can be controlled by altering media components.

In certain embodiments cells comprised by organoids of this disclosure exhibit increased expression of the CD40L surface marker compared to 2D culture controls.

In embodiments the disclosure comprises implanting an organoid of this disclosure into a human or non-human animal. In embodiments the disclosure comprises a non-human animal, such as a mammal, comprising an implanted organoid of this disclosure.

The following Examples are intended to illustrate but not limit various aspects of this disclosure.

Example 1

This Example provides a description of materials and methods used to produce results described in this disclosure. This description in this Example is expanded via specific but non-limiting implementations in Example 7.

Naïve B Cell Isolation and Engineered Stromal Cells.

GC formation in mice: For examining GC formation in vivo, C57BL6 mice were challenged with the T cell dependent antigen sheep red blood cells at 2% (Cocalico Biologicals, Inc). After 10 days, spleen were harvested to examine B-cell follicles for evidence of GC formation using immunohistochemistry (IHC), flow cytometry and immunofluorescence. IHC of paraffin-embedded serial spleen sections from mice were stained with CD45R/B220 (BD Pharmigen) for B cells and biotinylated peanut agglutinin (PNA, Vector Laboratories) for GC B cells as previously reported by us. For flow cytometry, splenocytes were isolated by a combination of mechanical and gradient separation methods (Fico/Lite-LM, Atlanta Biologicals) and stained with CD45R/B220 for B cells and GL7 and Fas (BD Pharmigen) for GC B cells. In these studies, CD45R/B220 was used for visualizing B cell throughout the lymphoid tissue. This B220 population may contain may contain CD19− population that induces follicular dendritic cell network formation as well as GC forming CD19+ cells. For germinal center phenotype, CD19+ B cell population was further analyzed for two conventional GC markers: GL7 and Fas. For organoid analysis, spleens were freshly obtained from C57BL6 mice as per institutional guidelines. B cells were obtained from splenocytes through negative selection using EasySep™ Mouse B cell Isolation Kit (Stem Cell Technologies) in accordance with manufacturer's protocol (yield ~90% CD19+). The 40LB cells, that express CD40L and produce BAFF, were generated as reported earlier by us and cultured in DMEM media (Life Technologies) with 10% FBS and 1% P/S. The 40LB cells were mitotically inhibited through incubation in cell culture medium containing 0.01 mg/mL Mitomycin C at 37° C. for 45 minutes in complete media conditions prior to the encapsulation. The cells were rinsed twice with 10 mL of 1×PBS before usage in the experiments.

Immune Organoid Fabrication.

Gelatin stock solution was freshly prepared by mixing gelatin powder (Sigma Aldrich) in RPMI 1640 medium followed by sterilization using syringe filter. Cells were mixed with warmed gelatin stock solution and diluted accordingly using cell culture medium. SiNP with 25-30 nm in diameter and 1 nm in thickness were obtained from Southern Clay Products Inc., USA. SiNP suspension was freshly prepared prior to the encapsulation procedure by mixing SiNP powder with deionized water and vortexing the resulting solution, followed by filtration through 0.22 μm syringe filters immediately before use. Organoids were fabricated in 96-well plates by first adding 5 μL of SiNP followed by injecting 5 μL cell-containing gelatin solution into the initial SiNP droplet, and then mixing the entire hydrogel through repeated pipetting. Each organoid was cured for approximately 10 minutes prior to addition of RPMI 1640 medium. Following the completion of fabrication step, the entire plate was placed in cell culture incubator for 1 hour before replacing cell culture medium in each well with that containing 100 ng/mL murine recombinant IL-4 (Peprotech). IL-4 stock solution was reconstituted in deionized water at 0.1 mg/mL concentration and kept as aliquots in −20° C. The medium was replaced every 3 days.

Material Characterizations.

Gelatin solutions of 2 and 4% (weight %) were prepared in PBS, mixed and vortexed with aqueous suspensions of SiNPs to obtain homogeneously cross-linked gels. All the modulus measurements were carried out for strain sweep (1-10% strain) at fixed frequency of 0.1 Hz, at 37° C. with rheometer (Anton Paar) equipped with 50 mm flat-plate geometry and gap of 50 μm. For scanning electron microscopy (SEM), samples were freeze dried and sliced into transverse sections by razor slitting. The sections were then sputter coated with Pt/Pd to provide conductivity. All the images were captured using Quanta 600 (FEI) at 20 kV equipped with energy-dispersive X-ray spectroscopy (EDS) detector (Oxford Instruments). The recorded EDS spectra were further analyzed by INCA software (Oxford Instruments) to confirm the presence of elements. For transmission electron microscopy (TEM) imaging of the SiNPs, approximately 5 μL volume of SiNPs in water was dropcasted onto a carbon-coated copper grid and air-dried. The images were captured under 200 keV voltage using JEOL JEM-2010 instrument (Japan). Bacterial endotoxin studies were performed using the US Food and Drug Administration (FDA) guidelines using limulus amebocyte lysate (LAL) assay.

Cell Extraction from Organoids.

Cell culture media was aspirated from each well. The organoid was washed once using 1×PBS and then incubated overnight in 10 U/mL collagenase solution (Worthington Biosciences) in cell culture conditions. The collagenase solution was prepared by reconstituting collagenase powder in serum-free RPMI 1640 medium. Following incubation, the organoid was disintegrated through pipetting and diluted in FACS buffer (1×PBS+/+with 10% FBS) for collagenase inactivation. The resulting cell suspension was passed through a 70 μm cell strainer to remove gel debris prior to flow cytometry analysis.

Immunofluorescence Microscopy and Flow Cytometry Analysis.

Immune organoids were incubated in rinsed and incubated in FACS buffer containing fluorescence-conjugated antibodies and/or live cell stains for 12 hours at cell culture conditions. The samples underwent three rinsing rounds with each one involving aspiration of old medium and incubation in fresh FACS buffer for 1 hour. Each organoid was covered with 1×PBS during imaging with Zeiss 710 confocal microscope (Zeiss). In all flow cytometry experiments we started with same number of naïve B cells, i.e. 20,000 B cells. At each time point, samples were degraded using collagenase and the entire cell suspension (regardless of final cell numbers) was re-suspended in equal volume for all samples and equally divided into 3 separate staining groups for flow cytometry analysis (to stain for CD19, GL7, Fas, IgM, IgG1, and IgE). The entire volume was analyzed for total number of cells. Extracted cells were stained by incubation in FACS buffer containing various combinations of antibodies with 1:1000 dilution for 45 minutes in the dark at 4° C. The antibodies consisted of: FITC-, APC, or PE-Cy7-conjugated anti-mouse CD19, GL7, Fas, CD40L, IgG, and IgM (eBioscience). FACS buffer was prepared using 1×PBS++ with 10% FBS. The cell suspension was rinsed twice using the same buffer prior to low cytometer using BD Accuri™ C6 flow cytometer. Data analysis was performed using FlowJo (Tree Star).

RGD Blocking.

B cells were incubated in FACS buffer containing blocker at specific concentrations for 30 minutes at 4° C. The buffer was prepared from 1×PBS and 10% FBS. In this experiment, cyclic RGD peptide (Cilengitide) was used with a final concentration of 10 or 50 µM in the blocking solution.

Statistical Analysis.

Analysis of variance (ANOVA) statistical analyses were performed using GraphPad Prism software with Tukey's test (1-way ANOVA) or Bonferroni correction (2-way ANOVA). A p-value of less than 0.05 was considered significant. Two tail t-test was performed for RGD inhibition analysis. All studies were performed in triplicates unless otherwise noted. All values are reported as Mean±S.E.M.

Example 2

Ex Vivo Engineered B Cell Follicle Organoid.

We first examined the structural organization of a secondary lymphoid organ by challenging C57BL6 mice with the T-cell dependent antigen sheep red blood cell and examined the B cell follicle and GC formation. Activated B cells in primary follicles proliferated rapidly to form GCs expressing Fas (tumor necrosis factor receptor superfamily member 6) and GL7 surface markers (FIG. 1A, B). Reconstructing from this model and the existing knowledge of dependency of lymphoid B cells on T cell-mediated CD40L and FDC-mediated B cell activating factor signaling, BALB/c 3T3 fibroblasts were stably transfected with both CD40L and B cell activating factor (called hereafter 40LB), as reported earlier by Nojima et al. (FIG. 1C). Primary B cells with 40LB stromal cells were co-encapsulated into an RGD-presenting nanocomposite hydrogels of gelatin ionically cross-linked with SiNP that were 20-30 nm in diameter and ~1 nm in thickness (FIG. 1D, E). While gelatin-based 3D hydrogels are known in the art, primarily as chemically modified system that require UV exposure (methacrylate functionalities), the present disclosure uses engineered hydrogels of polyampholytic gelatin that ionically interacts with the anisotropically distributed opposite charges on the synthetic SiNP resulting in hydrogels that remain stable and do not liquefy at 37° C. (FIG. 1E). Primary B cells were successfully encapsulated in these hydrogels and stained positive for Calcein after 24 hours of encapsulation (FIG. 1F).

Example 3

Organoid Material Properties Regulate the Spreading and Functional Behavior of Engineered Stromal 40LB Cells.

Figure 2:
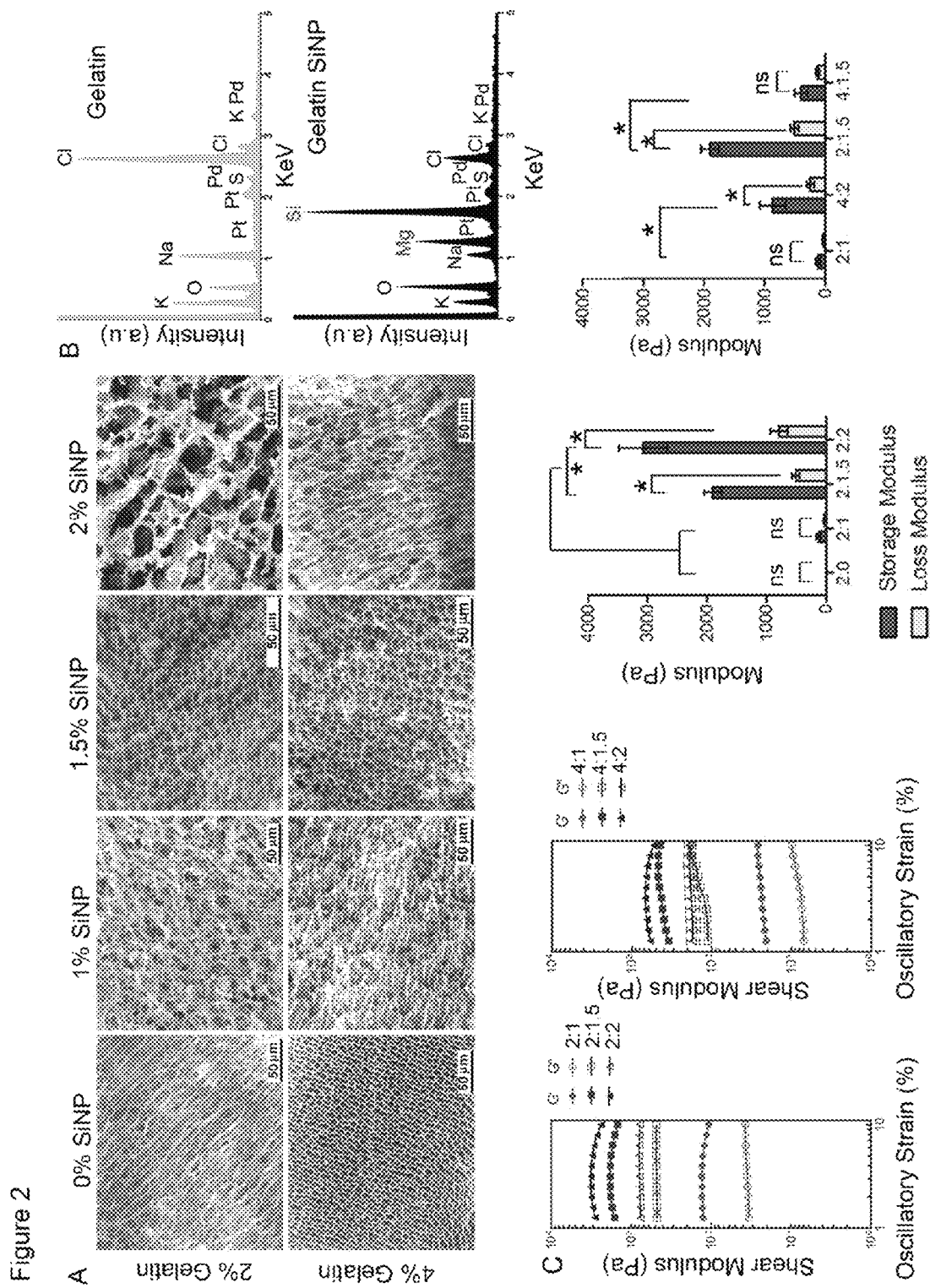
FIG. 2. Material characterization of immune organoids. (A) SEM analysis of hydrogel compositions with 2% and 4% gelatin with and without SiNP. (B) Energy-dispersive X-ray spectroscopy analysis in gelatin hydrogel with and without SiNP. (C) Rheological analysis on storage and loss moduli for 2% gelatin hydrogel with or without SiNP weight %. Mean±S.E.M, n=5, *P<0.05, ANOVA with post-hoc Tukey's test.

A criterion for material selection was the structural resemblance to the microarchitecture of compartments in the lymphoid tissue, which provides structural stability and yet allow for cell proliferation and dense stromal network formation (FIG. 1A). Using SEM, we evaluated the effect of SiNP concentration on hydrogel microarchitecture (FIG. 2A). Hydrogels with 2% gelatin and 1.5% SiNP resulted in more uniformly distributed porous structure in comparison to gelatin-only mixture, which could be attributed to the presence of charged surface in SiNP that would prevent the ionic aggregation of gelatin fibers with each other (zeta potential—28±3 mV vs. 4±0.4 mV, respectively). This observation is further supported by the marked decrease in pore size as gelatin concentration was raised from 2% to 4% while keeping SiNP concentration constant at 1.5%. The presence of SiNP in hydrogels was confirmed with EDS analysis according to known approaches that indicated the presence of Mg and Si peak only in SiNP cross-linked hydrogels but not in plain gelatin gels (FIG. 2B).

We analyzed whether, for immune organoid to be functional, the material stiffness should be in close proximity of the reported stiffness of secondary lymphoid organs (2300±1000 Pa). We determined the storage and loss modulus of hydrogels under physiological conditions (pH 7.4 and 37° C.) where gelatin remained liquid with no detectable storage and loss moduli, but the addition of SiNP resulted in cross-linked gelatin network increasing the organoid stiffness. As indicated in FIG. 2C, the storage modulus of the cross-linked network increased marginally to 130±40 Pa with incorporation of 1% SiNP ($p>0.05$), however increased significantly to 1900±50 Pa with 1.5% SiNP incorporation ($p<0.001$), which is closer to stiffness (storage modulus) of lymphoid tissues. Further increase in SiNP concentration to 2.0% resulted in substantial increase in hydrogel stiffness to 3100±410 Pa ($p<0.001$). Notably, the 2% gelatin hydrogel with 1% SiNP was fragile, which can be explained by a non-significant difference in storage and loss moduli ($p>0.05$). Using the same weight ratio (i.e. 2:1), 4% gelatin with 2% SiNP resulted in significant differences between G' and G" making the hydrogel stable ($p<0.05$). Interestingly, with the same SiNP weight percent, increase in gelatin weight percent from 2 to 4% resulted in an instable hydrogel network, which could be attributed to the excess uncrosslinked gelatin. This observation is further supported by the low storage modulus at 4% gelatin with 1.5% SiNP, with no significant differences between G' and G" ($p>0.05$).

Figure 3:
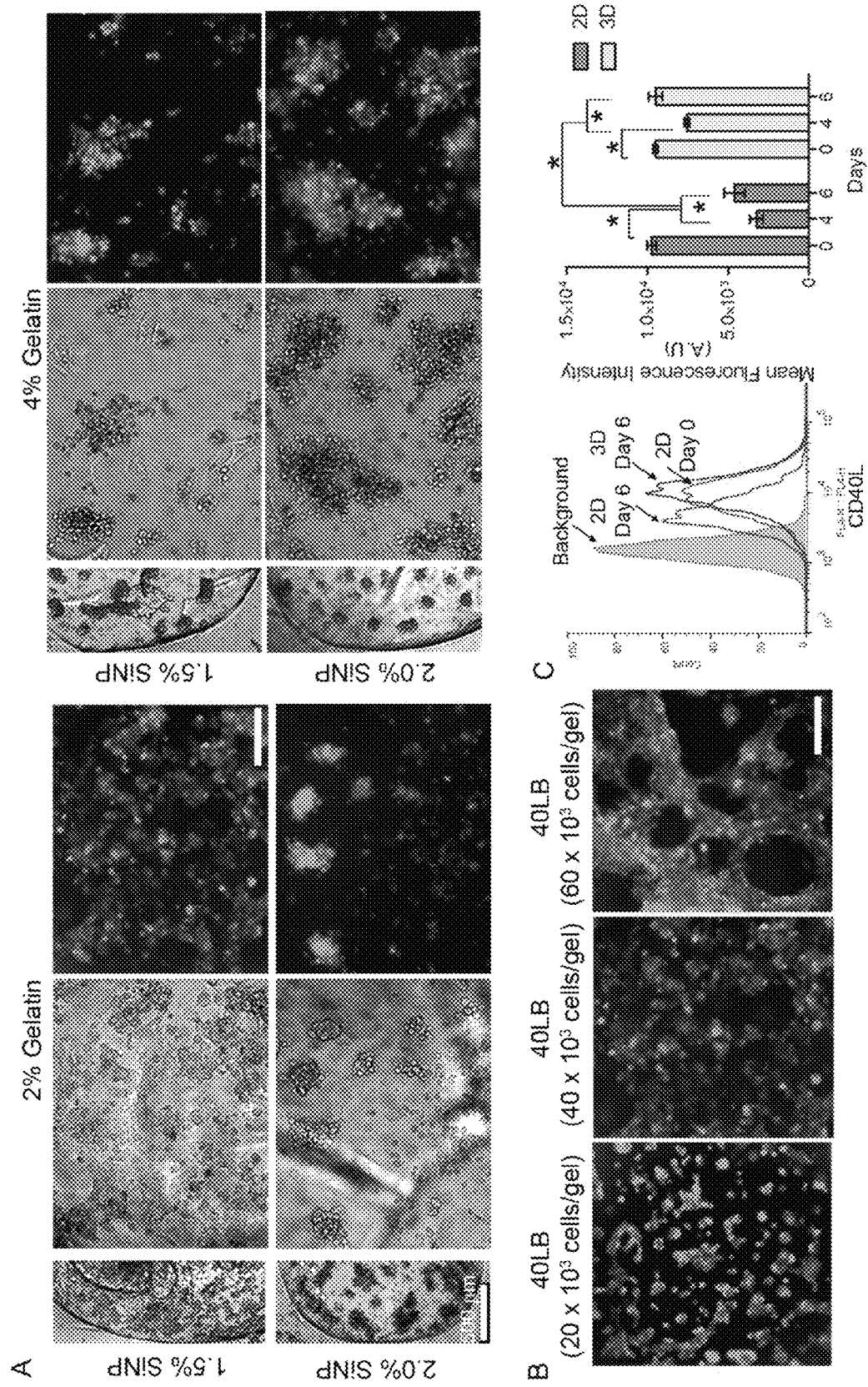
FIG. 3. Organoid stiffness affects 40LB stromal network and CD40L expression. (A) Fluorescence images of the 40LB stromal cell network formation with concentrations of gelatin and SiNP at 40,000 cells. Scale bar 200 µm (B) Fluorescence images of the 40LB stromal cell network formation with 2% gelatin and 1.5% SiNP and varying 40LB seeding density. Scale bar 200 µm (C) Histogram representing the overlay of CD40L expression for 2D culture of 40LBs on tissue culture plates versus 3D encapsulation in 2% gelatin with 1.5% SiNP organoids (Left). Bar graph representing mean fluorescence intensity of CD40L ligand expression in 2D and 3D cultures of 40LB (Right, Mean±S.E.M, n=4). *P<0.05, 2-way ANOVA with post-hoc Bonferroni correction.

To assess the influence of material composition toward network formation of 40LB cells, we encapsulated Cell-Tracker™ Green CMFDA stained 40LBs at 40,000 cells per hydrogel with increasing amount of gelatin or SiNP (FIG. 3A). By keeping the adhesive ligand density same (i.e. 2% gelatin), 40LBs demonstrated markedly more spreading with 1.5% SiNP than with 2% SiNP. Increase in adhesive ligand density to 4% gelatin resulted in marked clustering (FIG. 3A). We next examined the effect of seeding density of 40LB stromal cells within 2% gelatin hydrogels with 1.5% SiNP. As indicated in FIG. 3B, 20,000 seeding density formed small clusters over 48 hours whereas 40,000 cell seeding density resulted in tightly connected cellular network, and 60,000 cells formed a dense tubular-like network. These results clearly indicate that 2% gelatin with 1.5% SiNP present a stable hydrogel network that permits uniform cell spreading as a function of stromal cell density. Importantly, 3D encapsulation of 40LBs in these hydrogels resulted in a significantly higher ($p<0.001$) expression of CD40L surface marker compared to 2D cultures by day 6 of culture (mean fluorescent intensity 9500±430 AU for 3D cultured 40LB versus 4600±620 AU for 2D cultured 40LBs on tissue culture plastic surface), emphasizing the importance of 3D follicular niche (FIG. 3C). CD40L expression for 40LBs cultured in 3D was comparable to that observed with cells on day 0 (9500±150 arbitrary units). These observations clearly indicate that 2% gelatin with 1.5% SiNP had the most favorable 40LB response and supports our hypothesis that optimal stromal cell functioning is observed at hydrogel stiffness mimicking that of the native secondary lymphoid tissue.

Example 4

Figure 4:
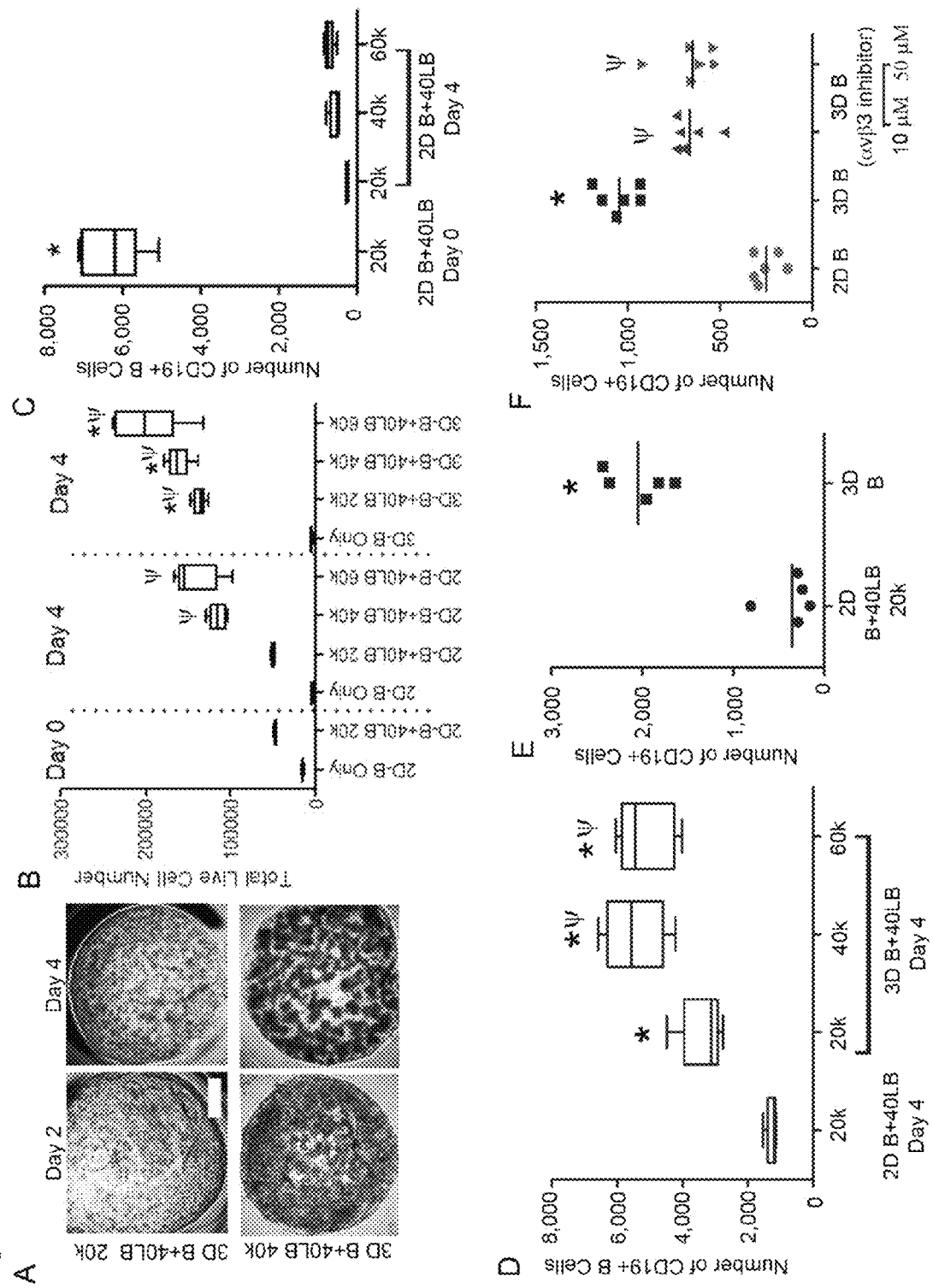
FIG. 4. Ex vivo proliferation of primary B cells within the immune organoid and role of integrins. (A) Phase images representing B cell proliferation within the organoids with varying number of stromal cells as a function of time. Scale bar: 500 µm. (B) Total number of viable cells on day 0 and 4. *P<0.05 w.r.t 2D groups on day 4 and □P<0.05 w.r.t day 0, 1-way ANOVA with post-hoc Tukey's correction. (C-D) Fold expansion plot of CD19+ cells in different matrix architectures (2D vs. 3D) and various 40LB cell amounts (20,000, 40,000, and 60,000) after 6 days in culture (Mean±S.E.M, n=5). Each hydrogel (10 µL) consisted of 20,000 naïve B cells and at the completion of study, harvested cells from each hydrogel were equally divided into 3 groups for analysis. *P<0.05 w.r.t 2D groups and □P<0.05 w.r.t 3D with 20,000 40LBs, 2-way ANOVA with post-hoc Bonferroni correction. (E) Number of CD19+ cells in 2D co-cultures with 40LB (n=5) and 3D organoids with no 40LB *P<0.05, t-test. (F) Number of CD19+ cells in 2D versus 3D systems after 2 days in the presence or absence of 10 or 50 µM Cilengitide (Mean±S.E.M, n=5). *P<0.05 w.r.t 2D groups and □P<0.05 w.r.t 3D without Cilengitide, t-test.

Ex vivo proliferation of primary B cells within the immune organoid and role of integrins. Based on our observation of dependency of 40LB cells on the biophysical characteristics and cellular compositions of the hydrogels, we expected the interaction between cells and the 40LB network to depend on stromal cell density. We next performed co-cultures of naïve B cells with 40LBs as a function of 40LB density in presence of 100 ng/mL IL-4. As indicated in FIG. 4A, we observed distinct regions of closely packed cells in hydrogels that morphologically resembled the proliferating GC inside the B cell follicle (FIG. 1A). Notably, this morphological appearance was a function of 40LB density and qualitatively indicated B cell follicle formation and high proliferation of B cells in the organoids, as observed in GC reactions in vivo. We next evaluated the total number of live cells using flow cytometry (Calcein+, FIG. 4B) and observed a significant increase in the number of viable cells over 4 days in our 3D organoids in comparison to 2D systems when B cells were co-cultured with 40LB in media supplemented with 100 ng/mL IL-4 ($p<0.05$).

Figure 8:
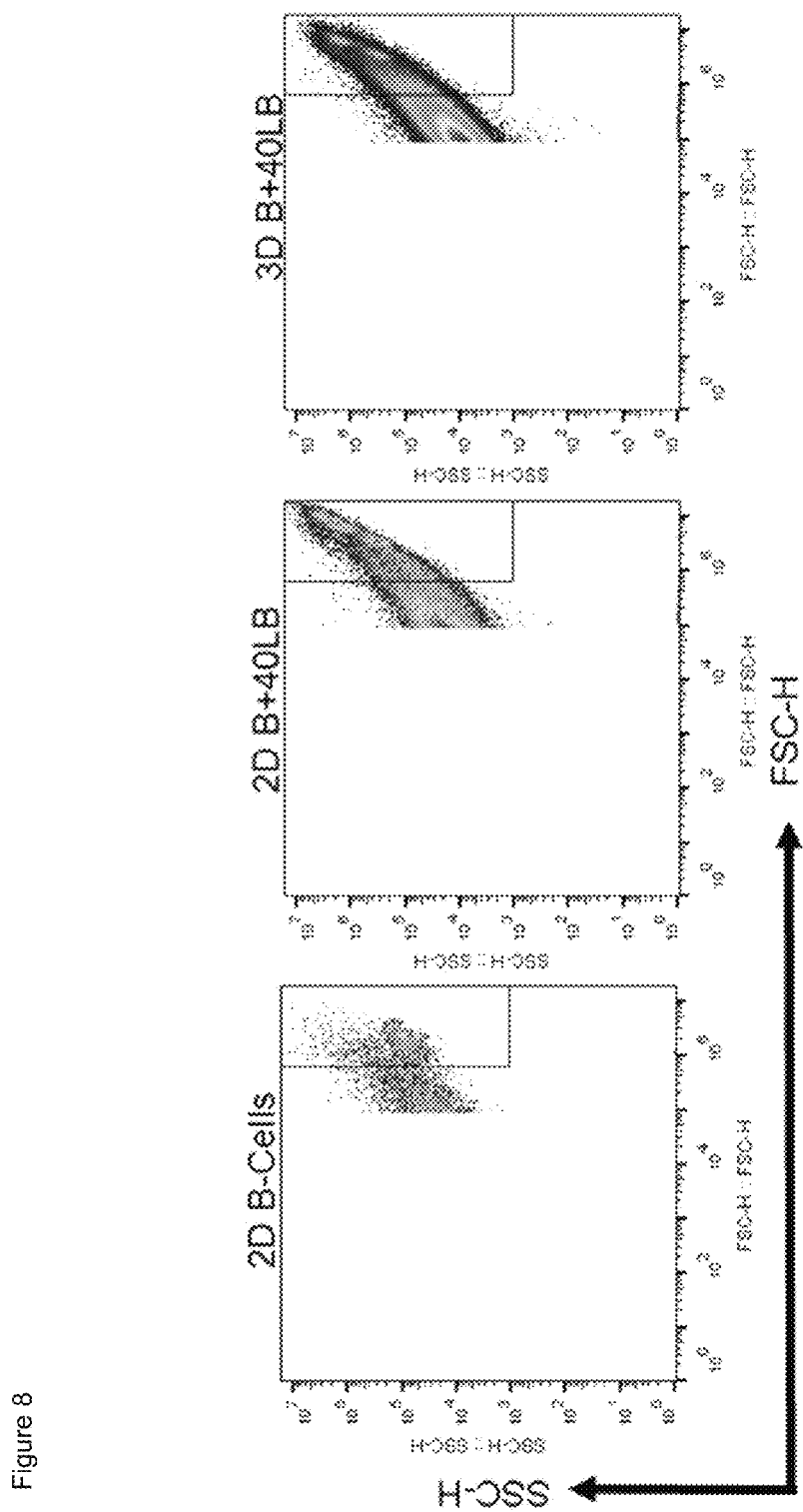
FIG. 8. Gating strategy for B cells in organoids. Nanoparticles have auto-fluorescence in the FL2 channel of the flow cytometer. Gating was done to separate SiNPs from APC-CD19+ B cells (FL4 channel). Numbers within gate represents number of CD19+GL7+ B cell for that particular group. Each plot is representative of n=5 hydrogels or 2D wells per group.
Figure 8:
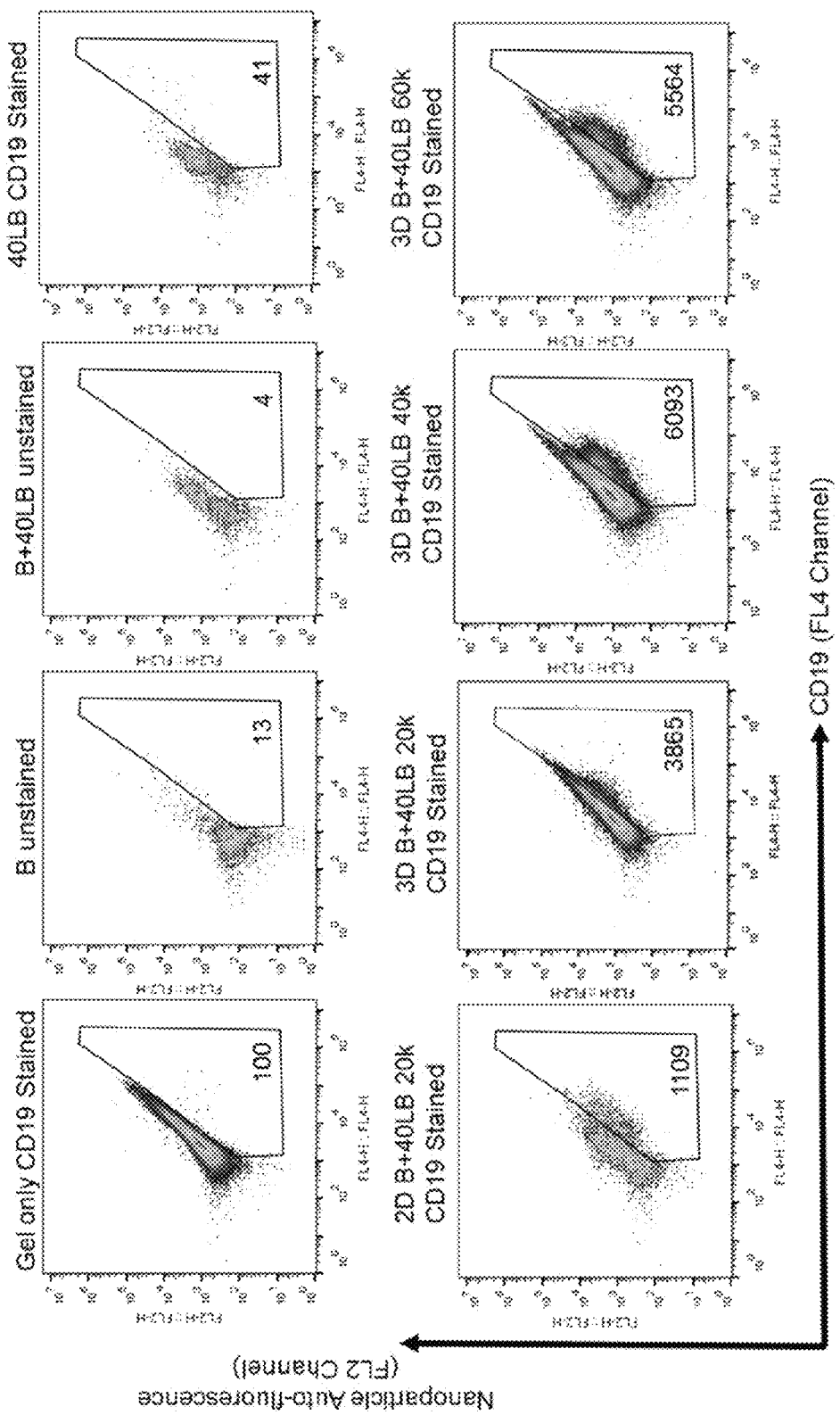

We analyzed 2D co-cultures for CD19+ B cells at 20,000, 40,000, and 60,000 40LB cells. Each condition included 20,000 naïve B cells and at the completion of study, the harvested cells were equally divided into 3 groups for further analysis. As indicated in FIG. 4C, the total number of CD19+ cells was significantly reduced in 2D cultures and there was no significant difference between any of the 40LB seeding densities. Therefore, 20,000 40LB cell seeding density was considered for further comparison. We determined the role of cell seeding density in 3D organoids and noted that the presence of 40,000 40LB cells in hydrogels resulted in maximum proliferation of CD19+ B cells over 4 days compared with other seeding densities within the 3D groups (Day 0: Naïve B cells 6500 cells; Day 4: 3D B+40LB with 40,000 40LBs resulted in 5477±477 cells versus 3D B+40LB with 20,000 40LBs resulted in 3390±295 cells and 2D B+40LB with 20,000 40LBs resulted in with 1261±72 cells; FIG. 4D and FIG. 8). These findings indicate that efficient stromal spreading and CD40L ligand binding interaction triggered the proliferation of CD19+ B cells. We evaluated the survival of CD19+ B cells after 2 days of culture in the organoids without any stromal support and observed a significant decrease in CD19+ B cell numbers in 2D co-culture compared to 3D B cell only cultures (FIG. 4E). Since gelatin has abundant RGD motifs, which are the cell attachment sites recognized by many integrins and lymphoid B cells bind to RGD domains, we blocked the RGD-mediated signaling using Cilengitide, a cyclic RGD pentapeptide that selectively inhibits $\alpha v \beta 3$ and $\alpha v \beta 5$ integrin binding to RGD. As indicated in FIG. 4F, we observed a partial but significant decrease in CD19+ B cells when blocked with Cilengitide, which at least confirmed the partial role of $\alpha v \beta 3$ and $\alpha v \beta 5$ integrins in supporting B cell survival in the organoids.

Example 5

Ex Vivo Induction into GC Reaction within the Immune Organoid.

Figure 5:
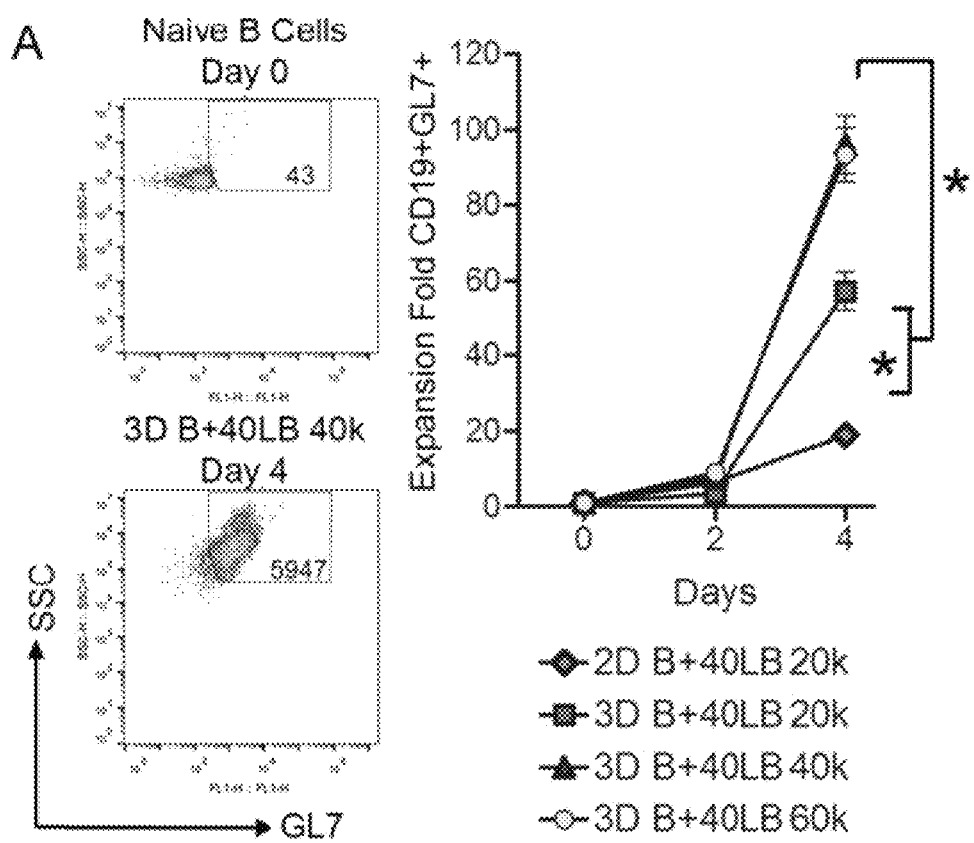
FIG. 5. Ex vivo induction into GC reaction within the immune organoid. (A) Fold increase in GC B cells (CD19+ GL7+) after 4 days in culture (Mean±S.E.M, n=5). Approximately fifty CD19+GL7+ cells were detected in naïve B cell population on day 0. Left panel represents scatter plot from flow cytometry with numbers indicating the GL7+ cells. *P<0.05, 2-way ANOVA with post-hoc Bonferroni correction. (B) Immunofluorescence analysis of GC B cells (CD19+GL7+) in the presence of 40LB stromal cells inside the organoid. (C) Number of CD19+GL7+GC B cells on day 4 after encapsulation in organoids of gelatin-SiNP or GelMA or cultured in 2D with SiNP (Bottom Panel, Mean±S.E.M, n=5). *P<0.05, ANOVA with post-hoc Tukey's test. (D) Gating strategy for GC phenotype analysis where CD19+ B cells were double stained with GL7 and Fas (Left Panel). Fold increase in the number CD19+GL7+ Fas+GC B cells on day 4 after encapsulation in organoids or cultured in 2D (Right Panel, Mean±S.E.M, n=5). *P<0.05, ANOVA with post-hoc Tukey's test.
Figure 5:
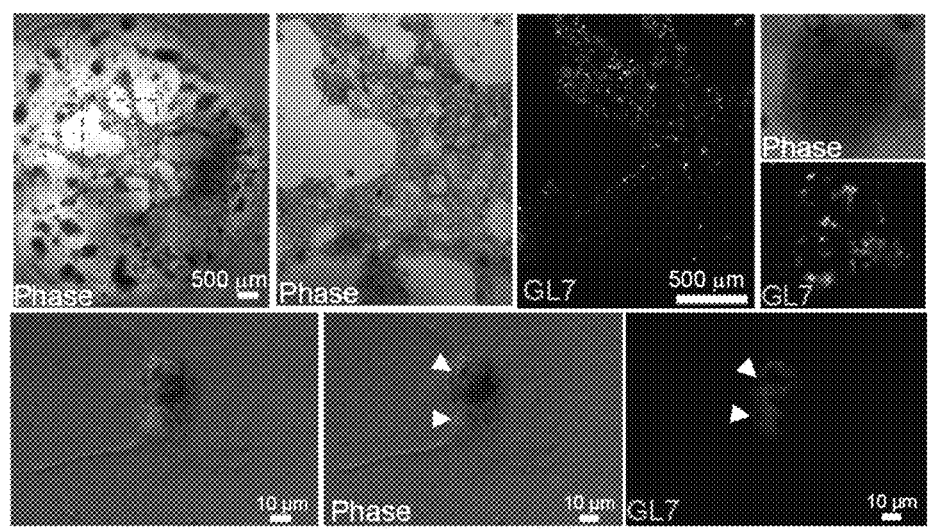
Figure 5:
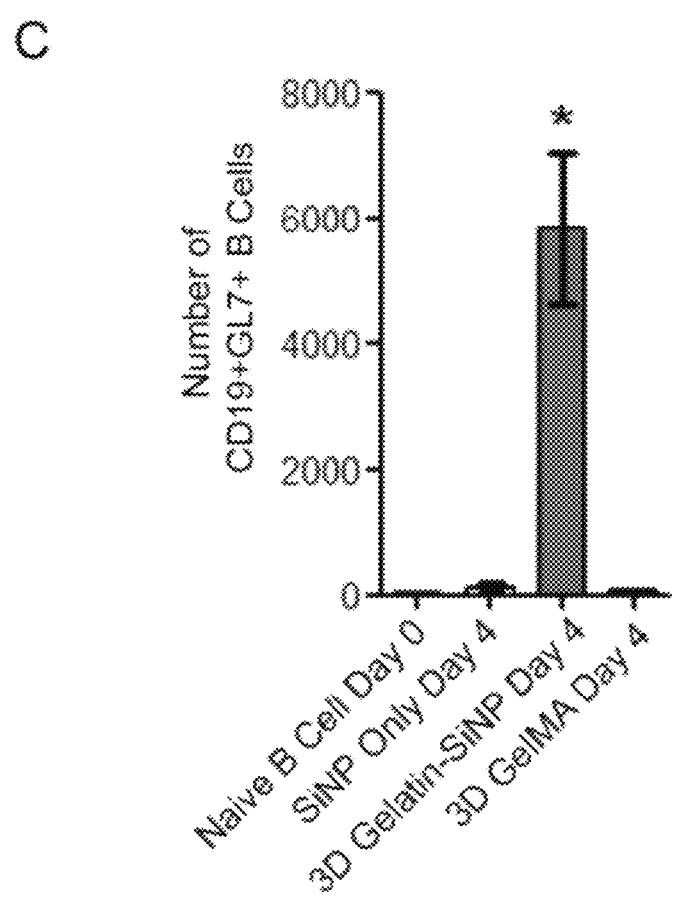
Figure 5:
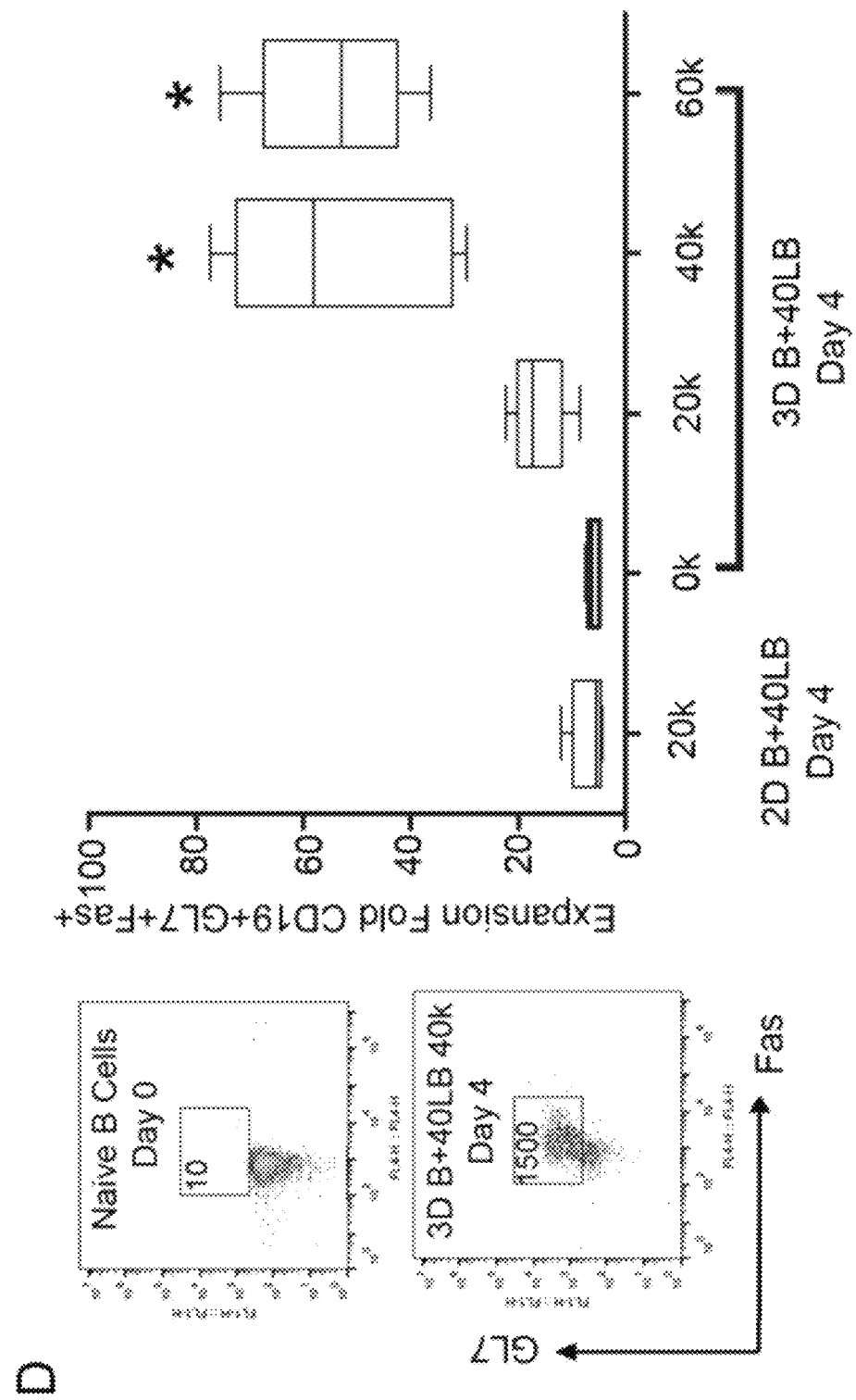
Figure 9:
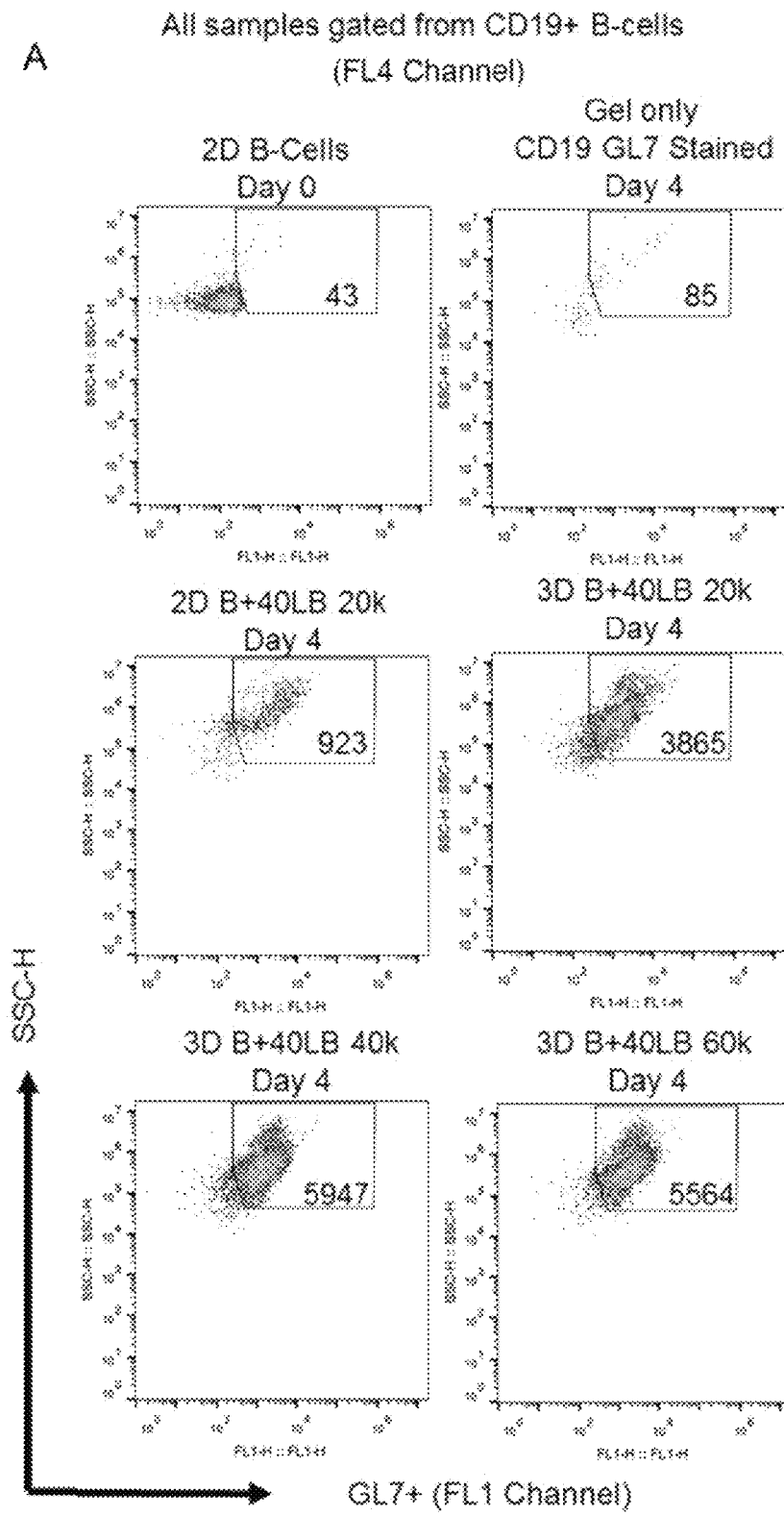
FIG. 9. Gating strategy for GC B cells in organoids. (A) Nanoparticles have auto-fluorescence in the FL2 channel of the flow cytometer. Gating was done to separate SiNPs from APC-CD19+ B cells (FL4 channel). Gated CD19+ cells were analyzed for FITC-GL7 staining. Numbers within gate represents number of CD19+ B cell for that particular group. (B) Gating was done to separate SiNPs from PE-Cy7-CD19+ B cells (FL3 channel). Gated CD19+ cells were analyzed for FITC-GL7 and APC-Fas staining. Numbers within gate represents number of CD19+GL7+Fas+ B cell for that particular group.
Figure 9:
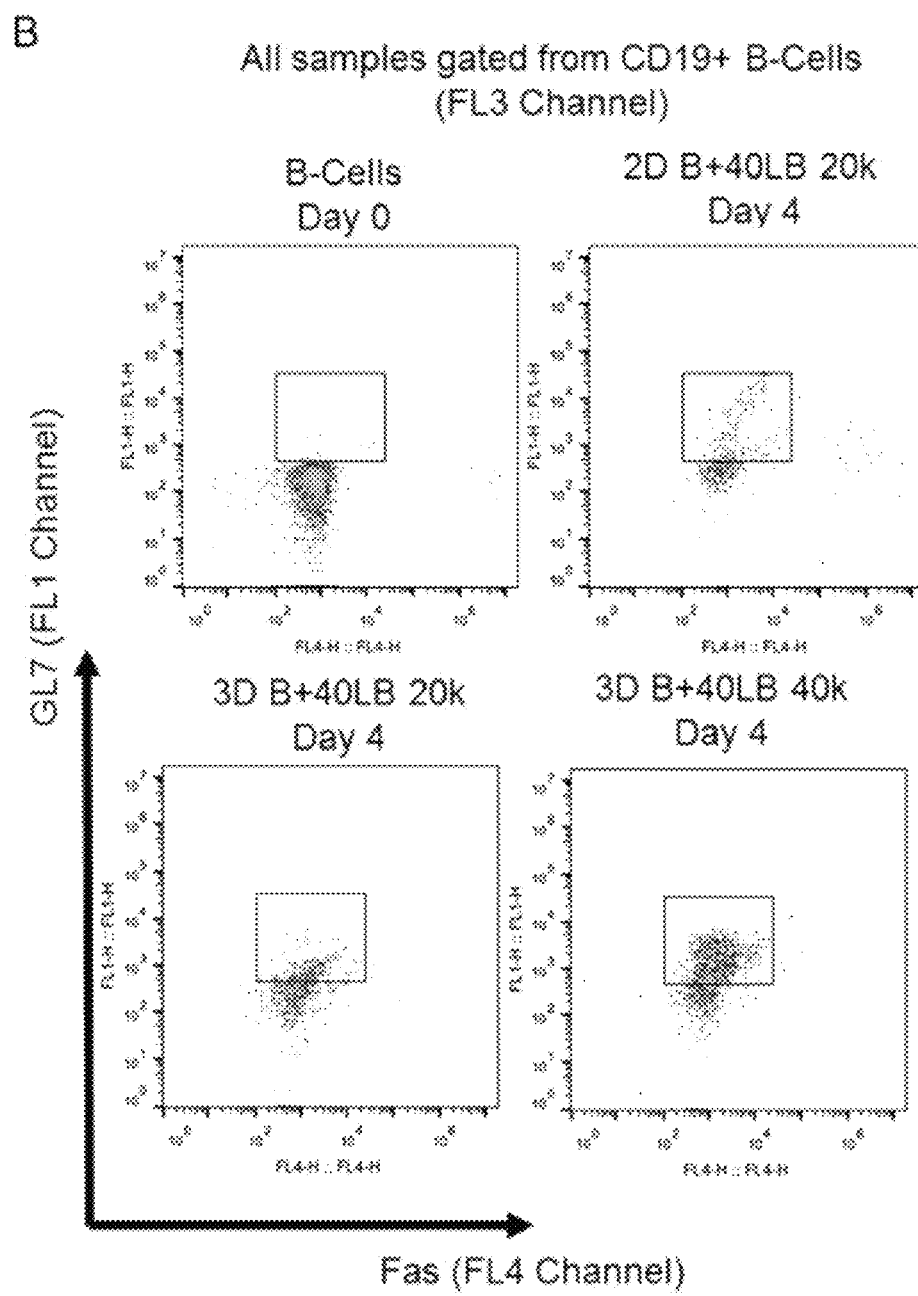

Notably, of these CD19+ cells, the organoid culture with B+40LB at 40,000 and 60,000 40LBs induced ~100-fold increase in GC-specific marker GL7 within 4 days compared to a 10-20-fold increase in 2D B+40LB co-culture (FIG. 5A and FIG. 9A). Within the 3D organoid cultures, the CD19+ GL7+ response was dependent on 40LB seeding density where organoids with 40,000 40LB induced 96±8 fold increase in CD19+GL7+ cell numbers that was significantly higher than 20,000 40LB group that induced 57±5 fold increase ($p<0.001$). There was no significant difference between 40,000 and 60,000 40LBs seeded organoids. These results were further confirmed by confocal studies that clearly demonstrate co-localization of GL7+ B cells on 40LB stromal network (FIG. 5B). We next analyzed GL7 expressing cells using SiNPs alone and gelatin organoids without nanoparticles using methacrylated gelatin (GelMA). GelMA is widely used in tissue engineering applications. As indicated in FIG. 5C, SiNP alone or GelMA failed to induce activation of GL7+ cells. In contrast, Gelatin-SiNP organoids induced significant generation of GC phenotype. These results emphasize the importance of 3D organoid and presence of SiNP in the organoids for efficient GC reaction. Since expression of Fas ligand (CD95) is a hallmark of GC B cells and important for their clonal selection, we next examined the expression profile of Fas within the CD19+ GL7+ cell population in the organoids and compared to the 2D co-cultures of B+40LB. As indicated in FIG. 5D and FIG. 9B, immune organoids with 40,000 and 60,000 40LB cells demonstrated a significant 55-fold increase in CD19+ GL7+Fas+ GC B cells compared to 2D B+40LB (7±1 fold) and 3D B+40LB co-cultures at 20,000 40LB cell density (16±2 fold). Despite the B cell proliferation phenotype, organoids with no stromal cells failed to induce GC B cells.

Example 6

Antibody Isotype Class Switching in the Immune Organoid.

Figure 6:
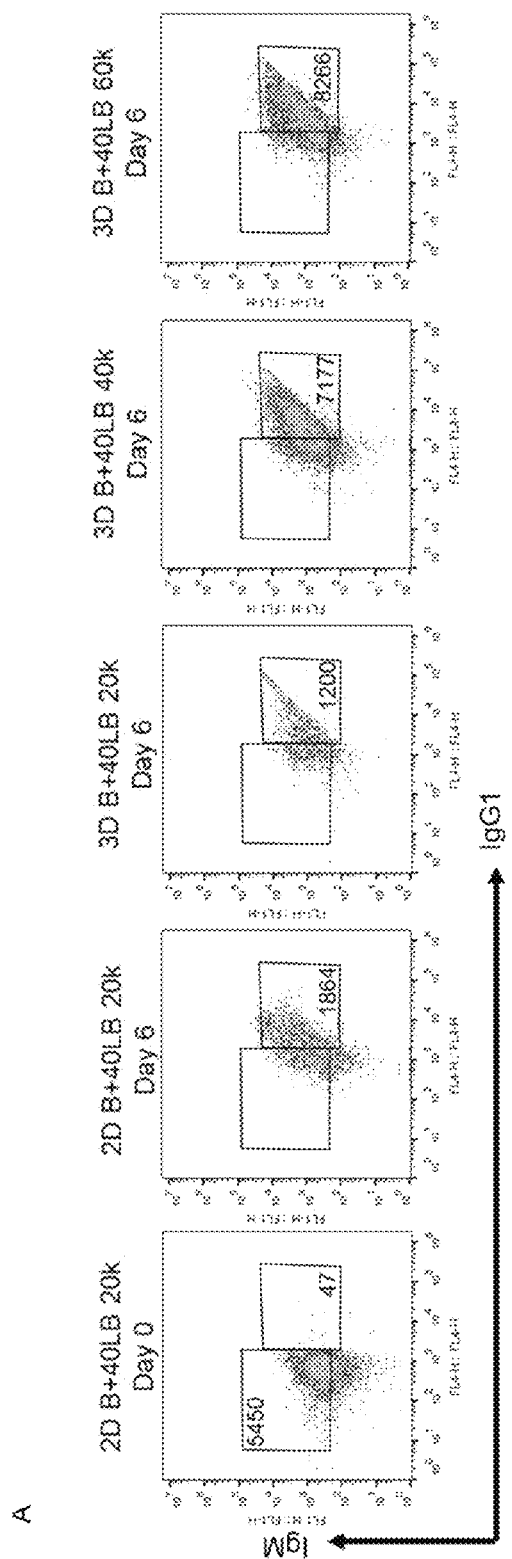
FIG. 6. Antibody Isotype class switching in the immune organoid. (A) Gating strategy for GC phenotype analysis where CD19+ B cells were double stained with IgM and IgG1. Naïve B cells on day 0 predominantly express IgM and no IgG1. (B) Increase in the number of CD19+IgG1+ B cells over 6 days in 3D immune organoids or 2D co-cultures. *P<0.05, 2-way ANOVA with post-hoc Bonferroni correction. (C) Number of CD19+ IgG1+ GC B cells on day 4 after encapsulation in organoids of gelatin-SiNP or GelMA or cultured in 2D with SiNP (Bottom Panel, Mean±S.E.M, n=5). *P<0.05, ANOVA with post-hoc Tukey's test. (D-E) Fold increase in the number CD19+IgG1+ B cells over 6 days in 2D culture. (D) Fold change for 2D B+40LB with 20,000 40LBs at 0, 10, and 100 ng/mL IL4. (C) fold change for 2D B+40LB with 20,000-60,000 40LBs at 100 ng/mL IL4; (Mean±S.E.M, n=5). (Mean±S.E.M, n=5, *P<0.05, 2-way ANOVA with post-hoc Bonferroni correction) (E) Bar graph represents a decrease in the number of CD19+IgM+ B cells on day 4 after encapsulation in organoids or cultured in 2D (Mean±S.E.M, n=5). *P<0.05, ANOVA with post-hoc Tukey's test.
Figure 6:
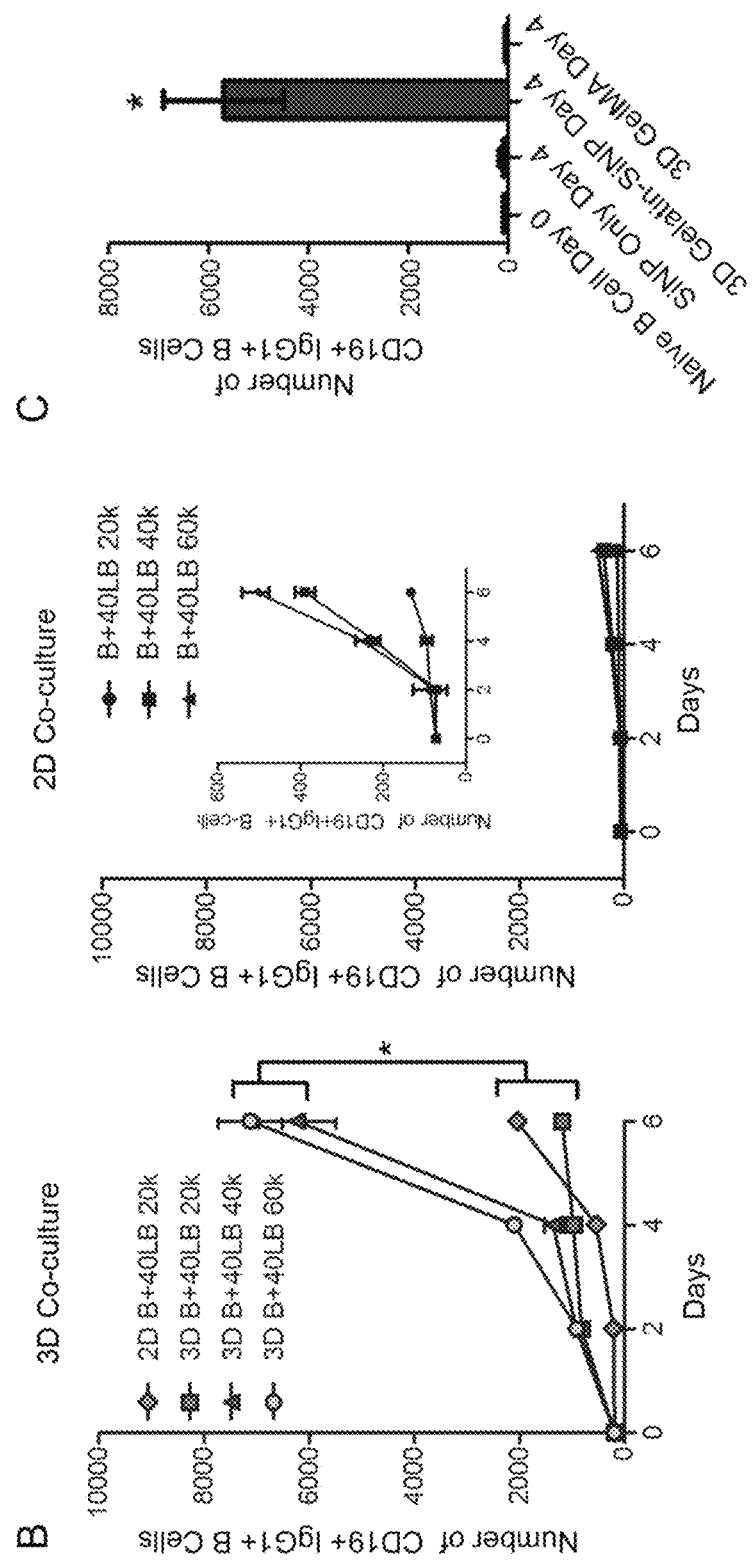
Figure 6:
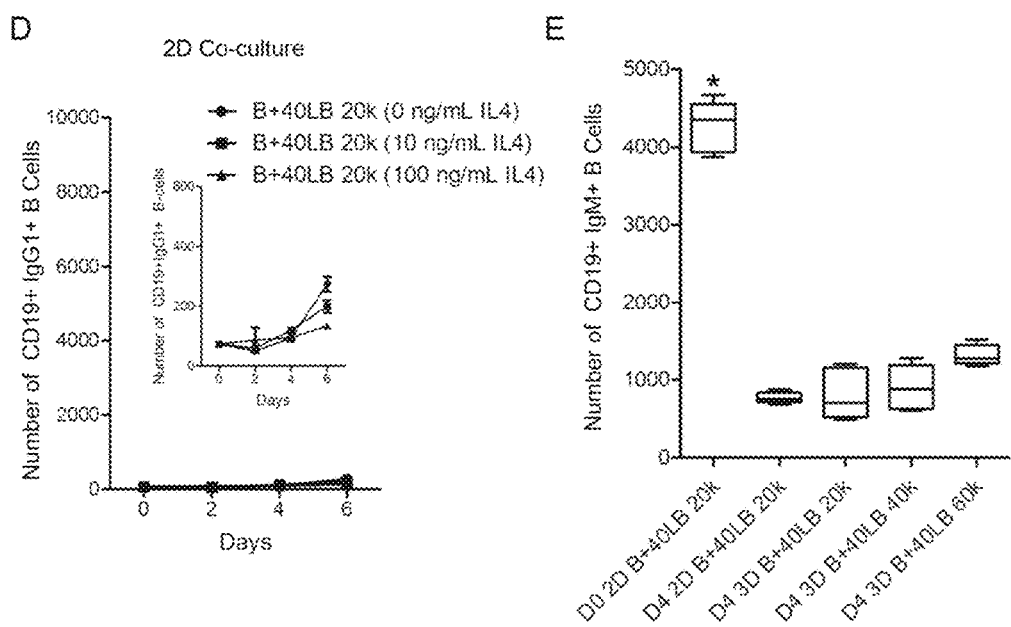
Figure 7:
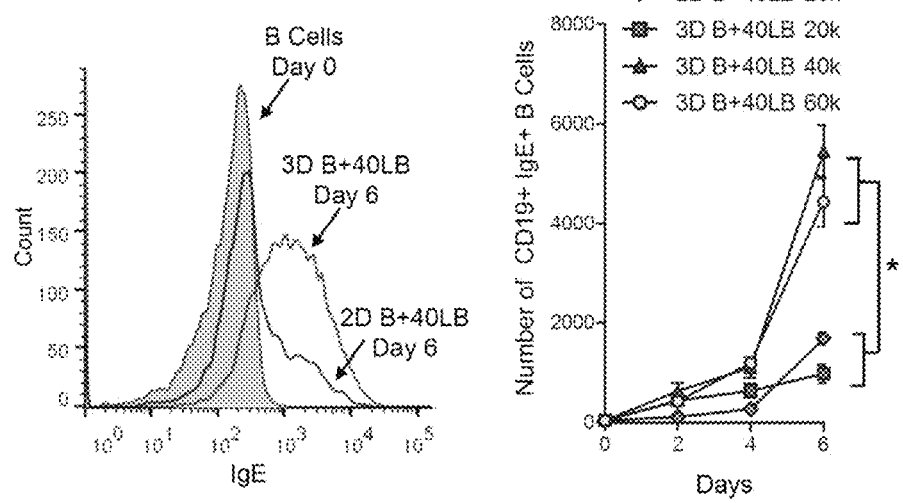
FIG. 7. IgE antibody expression in the immune organoid. Histogram representing the overlay of IgE expression for 2D and 3D co-cultures (Left). Increase in the number of CD19+ IgE+ B cells over 6 days in 3D immune organoids or 2D co-cultures (total 30-40 CD19+IgE+ B cells on day 0). (Mean±S.E.M, n=5, *P<0.05, 2-way ANOVA with post-hoc Bonferroni correction).

Another hallmark of GC reaction is the antibody class switching that occurs in GC B cells to produce antibodies with distinct effector functions. Activated B cells are known to undergo antibody class switching from IgM to IgG or other Igs. Recognizing that the 3D immune organotypic cultures induced a phenotypic GC reaction, we then tested its functionality by analyzing antibody class-switching from IgM to IgG1 and IgE compared. Using flow cytometry on cells extracted from the organoids, we observed a robust class switching where the number of IgG1+ B cells increased significantly from 185±14 cells on day 0 to 7120±612 cells on day 6 in 3D B+40LB organoids with 40,000 40LB cells (FIG. 6A,B). The cell numbers observed in 3D B+40LB organoids with 40,000 40LB cells were comparable to 3D organoids with 60,000 40LB cells. No such increase in CD19+IgG1+ B cells was observed in 2D B+40LB cultures with 40,000 and 60,000 40LB cells (FIG. 6C) or with GelMA (FIG. 6C) or with increasing concentration of IL-4 (FIG. 6D). The number of CD19+IgM+ B cells decreased significantly across all groups compared to day 0 (FIG. 6E). We next examined the levels of membrane-bound IgE expression and as indicated in FIG. 7, observed a marked shift in the mean fluorescence intensity of CD19+ IgE+ cells in 3D groups with higher 40LB seeding density on day 6 compared to 2D B+40LB on day 6 and naïve B cells on day 0. Quantitative analysis demonstrated a significant increase in the CD19+IgE+ level with 3D B+40LB organoids containing 40,000 40LBs (5446±536 cells) and 60,000 40LBs (4441±510 cells) as compared to 1687±116 cells observed with 2D B+40LB co-cultures (FIG. 7).

It will be recognized from the foregoing Examples and description that engineered ex vivo tissues for culturing primary immune cells and allowing them to interact with their microenvironment represents a powerful strategy to understand and manipulate immune cell behavior. However, and without intending to be bound by any particular view, it is believed that to date, no modular ex vivo B cell follicle has been developed with an ability to accelerate immune reactions through tunable design parameter. In contrast, in this disclosure we describe the development of 3D B cell organoids that phenotypically and functionally resemble the GC reaction in a secondary lymphoid tissue. The design of the immune organoid was based in part on structural, mechanical, and cellular composition of the secondary lymphoid organs. In this regard we determined that stromal 40LB cells demonstrated enhanced spreading and network formation when cultured in matrices with ~2000 Pa storage modulus and as a function of stromal cell density. This stiffness is closer to previously reported lymphoid tissue stiffness. Without intending to be constrained by any particular theory, it is considered that these findings explain a mechanism by which organoids support spreading of 40LBs which enables better cell-cell contact between stromal and B cells leading to superior B cell proliferation and activation.

Figure 10:
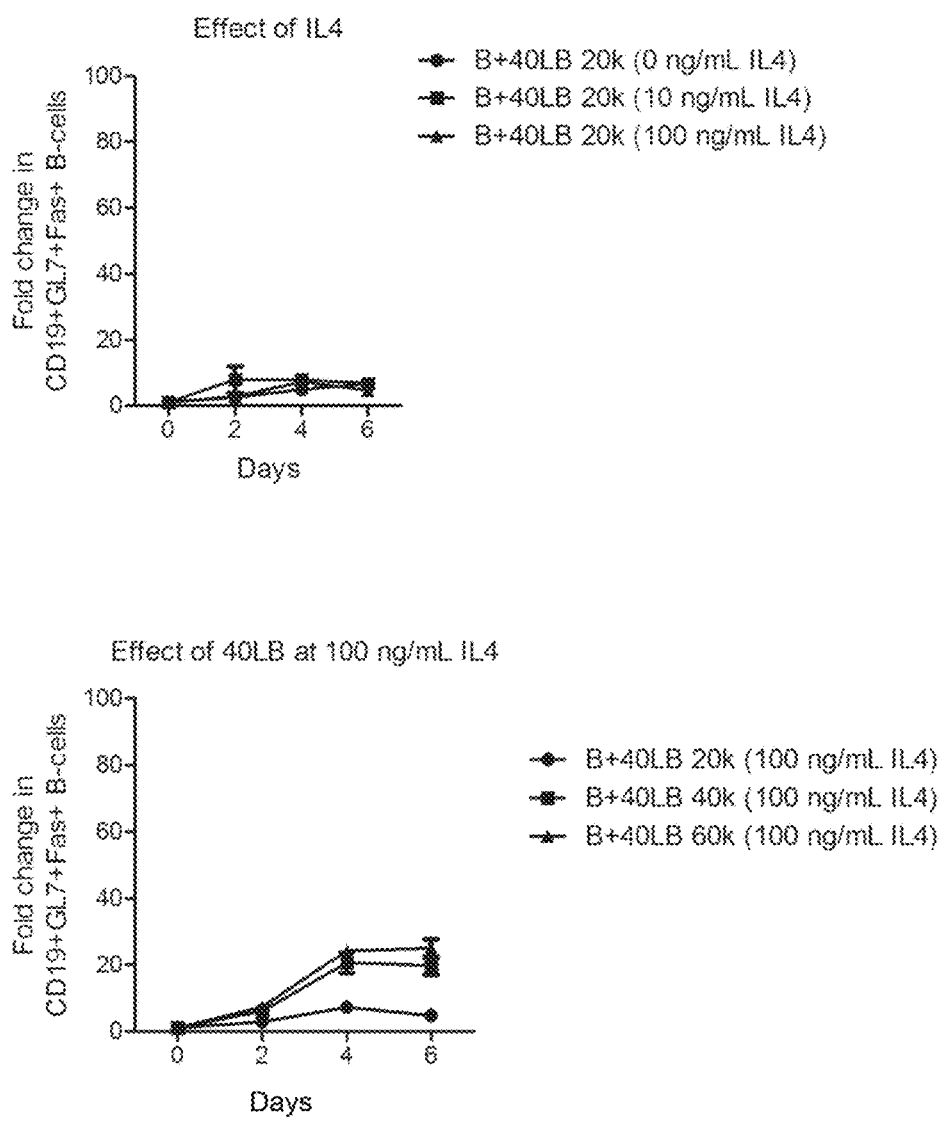
FIG. 10. 2D GC phenotype. Fold increase in the number CD19+GL7+Fas+ GC B cells over 6 days in 2D culture. Top panel represents fold change for 2D B+40LB with 20,000 40LBs at 0, 10, and 100 ng/mL IL4. Bottom panel represents fold change for 2D B+40LB with 20,000-60,000 40LBs at 100 ng/mL IL4. (Mean±S.E.M, n=5, *P<0.05, 2-way ANOVA with post-hoc Bonferroni correction).

It will be recognized in view of the results and description of this disclosure that compared to 2D co-cultures, 3D immune organoids as described herein can produce ~100-fold higher and rapid differentiation of naïve primary B cells to the GC phenotype with robust antibody class switching. To further establish the role of 3D ECM, stromal cell signaling and IL-4 in our observations, 2D B+40LB cultures were examined at 0, 10, and 100 ng/mL IL-4 and across 20,000-60,000 40LB seeding density. 2D cultures failed to efficiently induce the activation markers CD19+GL7+Fas+ across 0-100 ng/mL IL-4 (FIG. 10). At 100 ng/mL, increasing 40LB density to 40,000 and 60,000 cells resulted in a maximum of 20-fold appearance of GL7+Fas+ B cells, which was significantly lower than those observed with 3D cultures (55±6 fold, $p<0.001$, FIG. 10). These findings indicate that ECM, SiNP, and stromal signaling are important for induction of the GC phenotype in naïve B cells cultured in 3D organoids. The silicate nanoparticles used in this study to complex with gelatin are ultrathin nanomaterials, with a high degree of anisotropy and functionality. These two dimensional nanoparticles exhibit great potential in the field of regenerative medicine and drug delivery as they interact with biological entities in a substantially different manner than their respective 3D nano-counter parts because of their high surface to volume ratio. Synthetic silicates (such as $Na^+_{0.7}[(Mg_{5.5}Li_{0.3})Si_8O_{20}(OH)_4]^-_{0.7}$ used in this study) dissociate into nontoxic products ($Na^+$, $Mg^{2+}$, $Si(OH)_4$, $Li^+$) in aqueous conditions. Mg' plays a significant role in cellular adhesion via integrins. Lithium activates Wnt-responsive genes by inhibiting the glycogen synthase kinase-3[beta] activity via regulating Runt-related transcription factor-2 (RUNX2) activity. We determined that the observed effect was specific to the organoids and not any bacterial endotoxins. Observations from LAL assay indicate 0.01±0.001 endotoxin units (EU)/mL for SiNP alone and 0.04±0.01 EU/mL for gelatin-SiNP organoids, which are below the US FDA threshold of 0.5 EU/mL.

The present disclosure is suitable to facilitate the ability to drive GC reaction ex vivo at controllable and thereby reproduce immunological events with tunable parameters for better screening and translation of immunotherapeutics and other biotechnology avenues. Our natural gene rearrangement processes (somatic hypermutation and antibody class switching) are hallmark of antibody response to infections however could simultaneously lead to changes in a few genes involved in apoptosis and stress protection mechanism eventually leading to lymphoma in germinal centers. Therefore, biomaterials-based ex vivo immune organoids represent a new approach to study GC pathogenesis as in case of B cell malignancies and for rational screening of biotherapeutics against such malignancies, as further described above.

Example 7

This Example provides a description of particular and non-limiting implementations of the present disclosure. The disclosure includes each individual reagent, each individual step, and all combinations of reagents, and all combinations of steps, and all combinations of reagents and steps described in this example, and also includes all experimental parameters, such as all time periods, temperatures, weights, masses, concentrations, and the like. The disclosure also includes the proviso that any particular parameter can be expressly excluded from embodiments of this disclosure.

Comparison with In Vivo and Classic 2D Co-Cultures.

In vivo approaches to understanding immune cell development, functioning, and screening of immunotherapies against diseases. However in vivo approaches are costly with long turnaround times and do not allow for the control over the rate of immune reaction because the amount of extracellular and intracellular signals presented in vivo cannot be easily and precisely tuned in terms of magnitude and persistence. Although activation of B cells can be achieved ex vivo in 2D cultures through stimulation with antibodies (anti-Ig or anti-CD40), CD40L, cytokines, such as IL-4, the resulting cell growth is transient, with poor cell yield (a few 100 cells) and short term survival. As discussed above, and without intending to be bound to any particular view, it is believed that no 2D in vitro system has demonstrated the ability to modulate the extent of GC-like reaction or antibody class switching. As B cells (and lymphocytes in general) are prone to apoptosis in the absence of stimulatory signals, prior attempts have infected B cells with Epstein Barr Virus (EBV) for immortalization or using EBV-transformed cell lines. These EBV-transformed cell lines often lose their ability to produce antigen-specific antibodies when immortalized, therefore limiting the scope of these B cells. The present disclosure addresses these limitations.

Comparison with Existing In Vitro Lymph Node Tissue Engineering Approaches:

Current 3D scaffolds have only shown GC-like formation when implanted in vivo by exploiting the host microenvironment. For example, prior attempts have used collagen sponge scaffolds carrying a thymus-derived Lymphotoxin (LT)-β receptor and vascular cell adhesion molecule-1 (VCAM-1) expressing stromal cell line transduced to express murine lymphotoxin LT-α and used as an implantable scaffold for synthetic lymph node formation. When implanted in mice, the scaffold based organoid formed an organized secondary lymphoid-like structure with compartmentalized zones of B-cell and T-cell clusters, GCs, and networks of follicular DC. Another approach used a composite macroporous PEG hydrogel scaffolds infused with collagen to engineer a hydrogel mimicking a lymphoid organ to study immune cell migration. In another study, using colloidal crystal templating, interconnected arrays of porous hydrogel was formed. These PEG-gels, infused with collagen, promoted intra-scaffold migration of encapsulated T cells and DCs, with T cell migration dependent on the connecting pore size but no GC formation. However, these studies did not provide evidence of control over the rate of GC reaction ex vivo or in vivo, and it is believed prior to the instant disclosure that there have been no reports that demonstrate that differentiating B cells can survive ex vivo for successful conversion into GC or GC-like phenotype.

The organoid culture system of this disclosure comprises a 3D matrix adaptation of a co-culture system described above for in vitro generation of GC-like B cells. We encapsulated the relevant cells using the gelatin matrix that was crosslinked with silicate nanoparticles (SiNP). Adapting the protocol for a 96-well plate culture system enables establishment of a high throughout experiment platform to facilitate the improved generation of GC reaction, and/or to analyze test agents. In the Examples above, we have shown the ability of embodiments of this disclosure via (1) accelerated generation of GC-like CD19+ GL7+ B cells, (2) rapid formation of class-switched CD19+ IgG1+ B cells, (3) high number of CD19+ B cells, (3) integrin-mediated B cell survival, and (4) uniform stromal network formation. Notably, inhibition of gelatin-$\alpha v \beta 3$ integrin interactions by the use of a commercially available Cilengitide inhibitor resulted in partial reduction of B cell proliferation, which suggests the possibility of other integrin-gelatin interactions.

Experimental Design.

Figure 11:
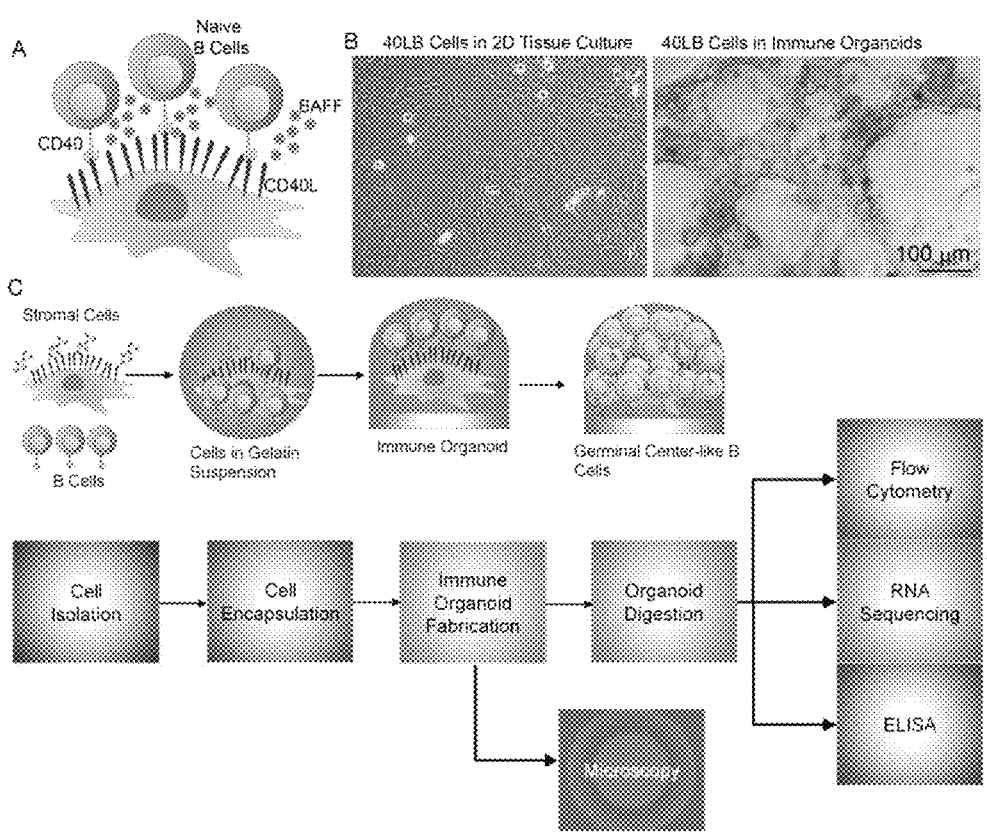
FIG. 11. Overview of Immune Organoid: (A) Interaction between primary B cells and 40LB stromal cells that presents membrane-bound CD40L and secrete soluble BAFF. B cell interact with CD40L by engaging CD40 surface receptor, (B) Microscopy images of 40LB stromal cells grown in 2D (left) and 3D immune organoids (right), (C) Schematic of immune organoid development process with GC-like B cell differentiation process occurring within the 3D setting over time (top panel) and the workflow for the organoid culture system along with the relevant biological assays (bottom panel).

Overview of the procedure: The following step-by-step protocol describes one illustrative embodiment of a process to establish the immune organoids (FIG. 11B, C). Those skilled in the art will recognize that aspects of this illustrative approach can be modified.

In a general embodiment (step 1-4) the isolation of mouse splenocytes, the purification of B cells, the material preparation, and encapsulation of cells into the organotypic culture is described. Human splenocytes can also be used. Organoids are cultured in cytokine supplemented cell culture medium that is replaced every 4 days. Cell extraction from the organoid (step 5-6) involves degradation of the organoid with collagenase, followed by staining the cell suspension with antibodies. This example also includes protocols for flow cytometry, imaging, and RNA isolation.

Culture Medium:

In this protocol, the immune organoids are grown in cell culture medium supplemented with serum and recombinant cytokine. In order to achieve successful GC reaction and organoid maintenance, medium containing freshly added cytokine prior to the medium addition/replacement time is used.

Mouse Age:

In order to establish the organoid, splenocytes are isolated from mice that are 6-8 weeks old and then negatively selected for obtaining purified B cells. Older mice can be used and we have tested mice aged 10-20 weeks with no observable change in the resulting activation and differentiation events. We have also successfully worked with both freshly isolated and cryopreserved splenocytes.

Control Samples:

The separation of cells SiNP (and gelatin hydrogel debris) is based on separating cells that are positive for specific cell surface markers from the auto-fluorescence of SiNPs observed in the FL-2 channel. In order to specifically stain for B cells and determine the purity of B cell population used, we utilize fluorophore-conjugated antibody against CD19. For specific staining of differentiated cells, we use additional antibodies targeted against GL7 and Fas for observing the formation of GC-like B cells or IgM and IgG1 for analyzing the generation of class-switched B cells. For staining controls, we utilized unstained, isotype, or single-color stained samples. The staining is performed in a fresh buffer containing fetal bovine serum as a blocking agent to prevent non-specific binding between cell surface markers and antibodies.

Cellular Analysis:

The cells extracted from the enzymatically degraded organoids can be stained using antibodies for direct analysis via flow cytometer or can be sorted into specific cell populations for downstream analysis such as RNA or DNA isolation. For the latter method, it may be necessary to pool cells from multiple organoids to achieve the sufficient cell number.

The following representative reagents can be used: RPMI 1640 Medium (Thermo Fisher Scientific, cat. no. 11875-093); DMEM: High Glucose (Thermo Fisher Scientific, cat. no. 11965-092); Fetal Bovine Serum (FBS): Qualified and US Origin (Thermo Fisher Scientific, 26140-079); Normal goat serum (ABCAM, cat. No. ab7481); Penicillin-Streptomycin (P/S): 10,000 U/mL (Thermo Fisher Scientific, 15140-122); Mitomycin C (Amresco, cat. no. J594-2MG); Recombinant Murine IL-4 (PeproTech, cat. no. 214-14); Gelatin from porcine skin (Sigma Aldrich, cat. no. G2500-500G); Laponite XLG (BYK); Phosphate Buffered Saline (PBS) at pH 7.4 (Thermo Fisher Scientific, cat. no. 10010-023); Collagenase Type 2 (Worthington Biochemical, cat. no. LS004174); RBC Lysis Buffer (G-Biosciences, cat. no. 786-650); EDTA (BDH, cat. no. BDH7950-2); EasySep Mouse B Cell Isolation Kit (STEMCELL Technologies, cat. no. 19854); Trypsin-EDTA 0.25% (Thermo Fisher Scientific, cat. no. 25200056); Dulbecco's Phosphate Buffered Saline with Calcium and Magnesium (PBS++) (Corning, cat. no. 21-030); DOTAP Liposomal Transfection Reagent (Roche, cat. no. 11202375001); HEPES (Thermo Fisher Scientific, cat. no. 15630080); Sodium Chloride (NaCl) (Sigma Aldrich, cat. no. 57653-250G).

The following representative equipment can be used: Heracell 240i $CO_2$ Incubator (Thermo Scientific, cat. no. 51026280); 1300 Series Class II Type A2 Biological Safety Cabinet (Thermo Scientific, cat. no. 1335); BD Accuri C6 Flow Cytometer (BD, cat. no. 653118); Sorvall Legend Xl Centrifuge (Thermo Scientific, cat. no. 75004221); Sorvall Legend Micro 17 Microcentrifuge (Thermo Scientific, cat. no. 75002431); EasySep Magnet (STEMCELL Technologies, cat. no. 18000); Water Bath (Thermo Scientific, cat. no. 11-100-49SH); Analytical Balance (Mettler Toledo, cat. no. 11144917); Hot Plate (Fisher Scientific, cat. no. 15-460-10Q); Vortex Mixers (Fisher Scientific, cat. no. 02215365); WaterPro PS Polishing Systems (Labconco, cat. no. 9000520); Falcon Cell Strainer: 70 µm Pore Size (Corning, cat. no. 352350); Acrodisc Syringe Filter: 0.2 µm Pore Size membrane (Pall, cat. no. 28143-310); Corning Costar Clear Polystyrene 96-well Plates Untreated (Corning, cat. no. 3370); Centrifuge Tubes: 15 mL Volume (VWR, cat. no. 89004-368); Centrifuge Tubes: 50 mL Volume (VWR, cat. no. 89004-364); Falcon Polystyrene Tubes with 12×75 mm Size and 5 mL Volume (Corning, cat. no. 60819-295); Snaplock Microtube: 0.6 mL Volume (Axygen Scientific, cat. no. MCT060C); Snaplock Microtube: 2 mL Volume (Axygen Scientific, cat. no. MCT200C); Parafilm (Bemis, cat. no. PM992); Eppendorf Research Plus Single Channel 0.1-2.5 µL Pipette (Eppendorf, cat. no. 3120000011); Eppendorf Research Plus Single Channel 2-20 µL Pipette (Eppendorf, cat. no. 3120000038); Eppendorf Research Plus Single Channel 20-200 µL Pipette (Eppendorf, cat. no. 3120000054); Eppendorf Research Plus Single Channel 100-1000 µL Pipette (Eppendorf, cat. no. 3120000062); Syringe with Luer-Lok Tip: 5 mL Volume (BD, cat. no. 309646); Syringe with Luer-Lok Tip: 10 mL Volume (BD, cat. no. 309604); Pipet Tips for 0.1-2.5 µL Pipette (VWR, cat. no. 89078-464); Pipet Tips for 2-20 µL and 20-200 µL Pipette (VWR, cat. no. 89079-458); Pipet Tips for 100-1000 µL Pipette (VWR, cat. no. 89003-422); Tissue Culture Plate: 6-well Format and Treated Surface (Corning, cat. no. 353934); Tissue Culture Plate: 96-well Format and Treated Surface (Corning, cat. no. 353227); Tissue Culture Plate: 60 mm Diameter and Treated Surface (Corning, cat. no. 353934).

The following approaches can be used to prepare reagents.

Splenocyte Isolation from Mice:

Collect spleen from mice and store it in the splenocyte isolation buffer (see section below). While it is preferred to use freshly isolated spleen for the organoid culture, we have successfully observed differentiation process into GC-like B cells using cryopreserved splenocyte (with 90% FBS and 10% DMSO) and/or spleens incubated overnight in lymphocyte culture medium at 4° C. If the cells are already undergoing apoptosis, it can impact the organoid culture. Thus, in an embodiment the disclosure uses a population of cells that are not undergoing apoptosis.

Stromal Cell Line:

Prepare the 40LB stromal cell line transfecting BALB/c3T3 fibroblasts first with the CD40L gene and then with the B cell activating factor (BAFF) gene using any method of choice. To generate a 40LB cell line, briefly, first, clone mouse CD40L cDNA into a pApuro2 expression vector and transfect into the BALB/c3T3 fibroblasts by lipofection. Following the transfection process, select puromycin-resistant stable clones (40L cells) and subsequently pick a clone on which naïve B cells proliferated most extensively in the presence of IL-4 for BAFF transfection. Clone mouse BAFF cDNA into a pCA-neo expression vector, which is a T7-tag-deleted variant of the pCAT7-neo expression vector, and transfect into the selected clone of 40L cells. Select G418-resistant clones (40LB cells) and expand for future use. While any transfection method can be used, the lipofection performed in this protocol utilized DOTAP Liposomal Transfection Reagent. Briefly, prepare DOTAP/nucleic acid mixture by combining 50 µL of 0.1 µg/µL DNA diluted in HBS buffer and 100 µL of 30% (v/v) DOTAP diluted in FIBS buffer. Incubate the DOTAP/nucleic acid mixture for 15 min at room temperature and add it into 6 mL of cell culture medium to prepare the transfection medium. Incubate the cells to be transfected with the transfection medium for 6 hr and select the transfected clone with antibiotic-supplemented medium. HEPES Buffer Saline (HBS) buffer is defined here as sterile-filtered cell-culture grade 20 mM HEPES solution with pH of 7.4 and 150 mM NaCl. CD40L expression and BAFF secretion should be evaluated on a regular basis. Human and murine CD40L and BAFF cDNA and amino acid sequences are known in the art.

Naïve B Lymphocyte Culture Medium:

Prepare RPMI 1640 medium with 10% FBS and 1% P/S by combining 45 mL medium with 50 mL serum and 0.5 mL antibiotics. Store the culture medium at 4° C. and prepare a small aliquot of medium to be warmed up prior to use in the experiments.

Stromal Cell Culture Medium:

Prepare DMEM medium with 10% FBS and 1% P/S by combining 45 mL medium with 50 mL serum and 0.5 mL P/S antibiotics. Store the culture medium at 4° C. and prepare a small aliquot of medium to be warmed up prior to use in the experiments.

Gelatin Stock Solution:

Prepare 6% (w/v) gelatin stock solution by dissolving 300 mg of gelatin in the lymphocyte culture medium. Mix the reconstituted gelatin by vigorous shaking, incubate in the water bath set at 37° C. for 15 min for complete dissolution, and centrifuge at 200 g for 5 min, at RT, for removing bubbles that appear due to the mixing process. Heat the gelatin solution for another 15 min and pass it through the syringe filter to sterilize the material. Aliquot the resulting sterile gelatin in 2 mL microtubes and store them at 4° C.

Silicate Nanoparticle (SiNP) Stock Solution:

Prepare 3% (w/v) SiNP stock solution by dissolving 30 mg Laponite XLG in 1 mL sterile $H_2O$ contained by a 2 mL microtube prior to use. Vortex the resulting solution at maximum speed for 1-2 min until the solution turns clear with no particle sticking on the tube wall. Use freshly made SiNP to create a set of 80-100 organoids.

Recombinant IL-4 Stock Solution:

Spin down the tube containing lyophilized IL-4 at 10,000 g for 1 minute and add sterile 0.1% BSA solution to prepare 0.1 mg/mL IL-4 stock solution. Aliquot the cytokine solution and keep them at −20° C. for long-term storage.

Mitomycin C Stock Solution:

Add sterile PBS into the vial containing mitomycin C powder to prepare 1 mg/mL mitomycin C stock solution. Aliquot the solution and store them at −20° C. for long-term storage. Protect the solution from light throughout the entire process.

Splenocyte Isolation Buffer:

Prepare splenocyte isolation buffer with PBS++ containing 2% FBS, 1% P/S, and 5 mM EDTA. The buffer can be made by mixing 40 mL PBS++ with 800 µL FBS, 400 µL P/S, and 800 µL EDTA. Keep the buffer at 4° C. for long-term storage.

B Cell Purification Buffer:

Prepare B cell purification buffer with PBS containing 2% FBS, 1% P/S, and 1 mM EDTA. The buffer can be made by mixing 40 mL PBS++ with 800 µL FBS, 400 µL P/S, and 160 µL EDTA. Keep the buffer at 4° C. for long-term storage.

Collagenase Stock Solution:

Prepare syringe-filtered 10 U/mL collagenase II solution in serum-free RPMI medium. Incubate collagenase powder at room temperature for 15 min, weight 2 mg collagenase, and place it in a 2 mL microtube. Prepare 1000 U/mL concentrated collagenase solution by adding serum-free RPMI into the tube, mixing the solution gently via pipetting and inversion, passing the solution through syringe filter, and diluting it with additional serum-free medium to reach a final concentration of 10 U/mL. Store the solution at −20° C. for no more than 1 week.

Fluorescence Activated Cell Sorting (FACS) Buffer:

Prepare FACS buffer with PBS++ containing 2% FBS and 5 µM EDTA. The buffer can be made by mixing 40 mL PBS++ with 800 µL FBS, 400 µL P/S, and 0.8 µL EDTA. Store the buffer at 4° C. for long-term use.

Isolating Splenocytes from Murine Spleens (can be Performed in 40-60 min)

1. Place cell strainer on top of a 50 mL centrifuge tube (FIG. 12A).
2. Put 5 mL of splenocyte isolation buffer into the tube
3. Put a freshly isolated spleen on top of the strainer. Ensure that the spleen is placed in the middle of the strainer such that the cell suspension/slurry from spleen will not get stuck on the side part of strainer
4. Wet the cell strainer by rinsing with 5 mL of splenocyte isolation buffer
5. Mesh the spleen with the plunger of a 10 mL syringe
6. Flush the dissociated spleen with 10 mL splenocyte isolation buffer. Ensure that thorough washing is performed such that no spleen suspension is stuck to the strainer
7. Centrifuge the cell suspension at 200 g for 5 min, at RT, and re-suspend the splenocyte in 10 mL of RBC lysis buffer
8. Incubate in the dark at room temperature for 10 min. Centrifuge the cell suspension at 200 g for 5 min, at RT. Observe that the cell pellet has turned white to ensure that the red blood cell lysis is complete. Repeat the process if red streak is still visible at the top part of the cell pellet.

9. Re-suspend the splenocytes with 5 mL splenocyte isolation buffer. Ensure that there is no cell clump and pass the splenocyte through a cell strainer if any cell aggregates is seen in the solution)

Purifying B Cells from Whole Splenocytes (can be Performed in about 20 min)

10. Centrifuge the cell suspension at 200 g for 5 min, at RT
11. Resuspend the splenocyte with 0.5 mL B cell purification buffer
12. Move the cell suspension into a 5 mL polystyrene tube
13. Add 25 µL of normal rat serum and 25 µL of EasySep Mouse B Cell Isolation Cocktail
14. Mix gently and incubate for 10 min
15. Vortex the EasySep Streptavidin RapidSpheres for 30 sec such that complete mixing occurs and the solution looks uniform with no separation between the beads and the solution
16. Add 37.5 µL of EasySep Streptavidin RapidSpheres
17. Mix gently and incubate for 2.5 min
18. Add 1.6 mL B cell purification buffer to have ~2.5 mL for the final volume
19. Mix the cell suspension gently and place the tube inside the magnet and incubate for 2.5 min
20. Gently transfer the cell suspension into a new tube Preparing Feeder Layer Using 40LB Stromal Cells (can be Performed in about 60 min)

21. Prepare 0.01 mg/mL mitomycin C solution by mixing 120 µL of the stock solution with 12 mL of stromal culture medium. Dissolve the stock thoroughly because mitomycin C powder can fall out from the solution during storage and multiple pipetting can be needed to mix it with the cell culture media
22. Prepare two 100 mm tissue culture plates of confluent stromal cell culture with 90-95% confluency
23. Replace the cell culture medium of the 40LB stromal cells by aspirating the supernatant and gently adding fresh stromal medium that contains mitomycin C
24. Incubate the cells at cell culture conditions for 45-60 min
25. Carefully remove culture medium containing mitomycin C and store in a designated waste bottle
26. Wash cells with 10 mL PBS and store the first wash into the mitomycin C waste bottle
27. Wash cells with 10 mL PBS for the second time and aspirate the buffer as usual
28. Detach the cells by adding Trypsin and incubating them for 6 min
29. Deactivate the trypsin with serum-supplemented stromal culture medium and store the cell suspension in a clean new tube
30. Keep the suspended stromal cells in 4° C. until needed Establishing Immune Organoids Using Primary Murine B Cells and Gelatin Matrix (can be Performed in 60-80 min for 60 Organoids)

31. Place a glass beaker filled with water on a hot plate and set the heating dial such that the water temperature is maintained around 37° C.
32. Heat gelatin using the warmed water in the beaker until the gelatin is flowing
33. Mix cells with gelatin such that the resulting solution has 5% (w/v) gelatin+4,000 B cells/µL+8,000 40LB stromal cells/µL. Gently mix the cell-gelatin suspension such that uniform mixing is achieved without the formation of air bubbles which can reduce the effective amount of material that can be used in the organoid making process. It is important to maintain the organoid composition at 1.5% SiNP with 2% gelatin (w/v) because this composition results in robust spreading of 40LB cells, which is important for expression of CD40L and cell-cell interactions. For maximum B cell proliferation and differentiation, encapsulate 40,000 or higher seeding density of 40LBs per organoid. As discussed above, we observed that 20,000 cells/organoid formed small clusters over 48 hr whereas 40,000 and 60,000 cells/organoid resulted in dense, tightly connected cellular network. Clustering of 40LB cells can reduce the proliferation and differentiation of B cells, while at the same time provide a control over the kinetics of B cell reaction.

Figure 12:
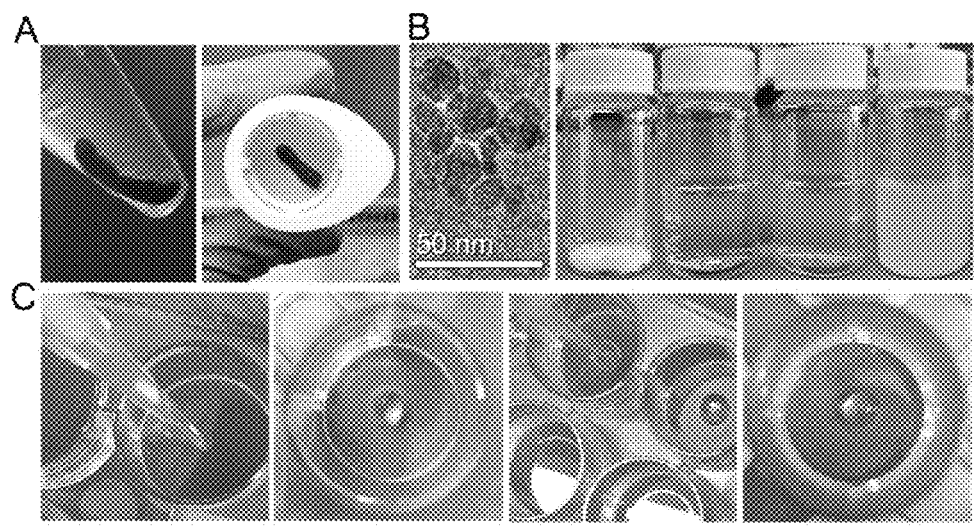
FIG. 12. Organoid Preparation Process: (A) Mouse spleen stored in buffer after isolation (left) and placed inside a cell strainer prior to homogenization (right), (B) visual image of SiNP (left) and silicate nanoparticle preparation process (right) from the SiNP powder form (first), addition of water (second), formation of clear homogenous SiNP solution upon vortexing (third), and appearance of cloudy suspension prior to addition of water into SiNP powder, and (C) generation of organoid by preparing SiNP droplet inside the well (first and second), injecting gelatin solution into the first droplet (third), and appearance of the formed organoid hydrogel that stay intact at cell culture condition (fourth).

34. Keep the resulting cell suspension on ice
35. Prepare 3% (w/v) SiNP stock solution and vortex the nanoparticle suspension in water (FIG. 12B). Prepare the SiNP stock solution prior to the cell encapsulation process. Preparing SiNP can take time and leaving cells in gelatin suspension outside of 37° C. incubator can induce apoptosis in B cells. Vortex SiNP solution until the particles are fully dissolved. Failure to achieve complete dissolution can result in clumps of nanoparticles.
36. Keep the resulting nanoparticle solution at room temperature
37. Prepare 10 ng/mL IL-4 solution by mixing 2 µL of the thawed IL-4 stock solution with 20 mL of lymphocyte culture medium
38. Heat the cell-gelatin suspension for 2 min using the warmed water until gelatin starts flowing. This step can be checked by inverting the tube and seeing that the gelatin suspension can move quickly
39. Mix the cell-gelatin suspension to ensure that cells are homogenously mixed and not settled. Mix gently without forming the bubbles and repeating the process after encapsulating cells in 4-5 organoids.
40. Pipet 5 µL SiNP solution into the middle of each well as a droplet (FIG. 12C)
41. Pipet 5 µL of the cell-gelatin suspension into each SiNP droplet
42. Place the pipette tip in the middle of each droplet and pipet gently 3-5 times to mix the solution; ensure that the tip is in the middle of the droplet such that efficient mixing can occur and most cells are contained within the droplet.
43. Keep the cell-gelatin suspension warmed throughout the organoid fabrication process
44. Incubate the fabricated organoid at room temperature for 10 min to complete the curing step
45. Add 200 µL cytokine-supplemented lymphocyte culture medium into each well
46. Repeat the last few steps to continue making the next set of organoids
47. Replace the medium with a fresh one every 4 days Dissociating Organoids to Extract the Cells for Cellular Analysis (can be Performed Overnight for Step 49 and 90 min for Step 50-53)

Aspirate the medium from each well and wash each organoid with 200 µL of PBS. Perform both aspiration and rinsing gently to avoid perturbing the organoid, this can be done by placing the pipette tip at the well wall and pipetting slowly 48. Place 200 µL of collagenase solution into each well
49. Incubate the collagenase-covered organoid overnight in the $CO_2$ incubator (5% $CO_2$ and 37° C.) to ensure a thorough enzymatic degradation process
50. Pipet the supernatant 5-10 times to dissociate the organoid. Perform the pipetting so that it is directed toward the center of organoid to ensure that the mechanical perturbation degrades most of the construct)
51. Pass the cell suspension across a cell strainer to remove large debris.

Cell Staining for Flow Cytometry (can be Performed in 90 Min for Step 54-59; 120 Min for Step 60-61 for 60 Organoids)

Figure 14:
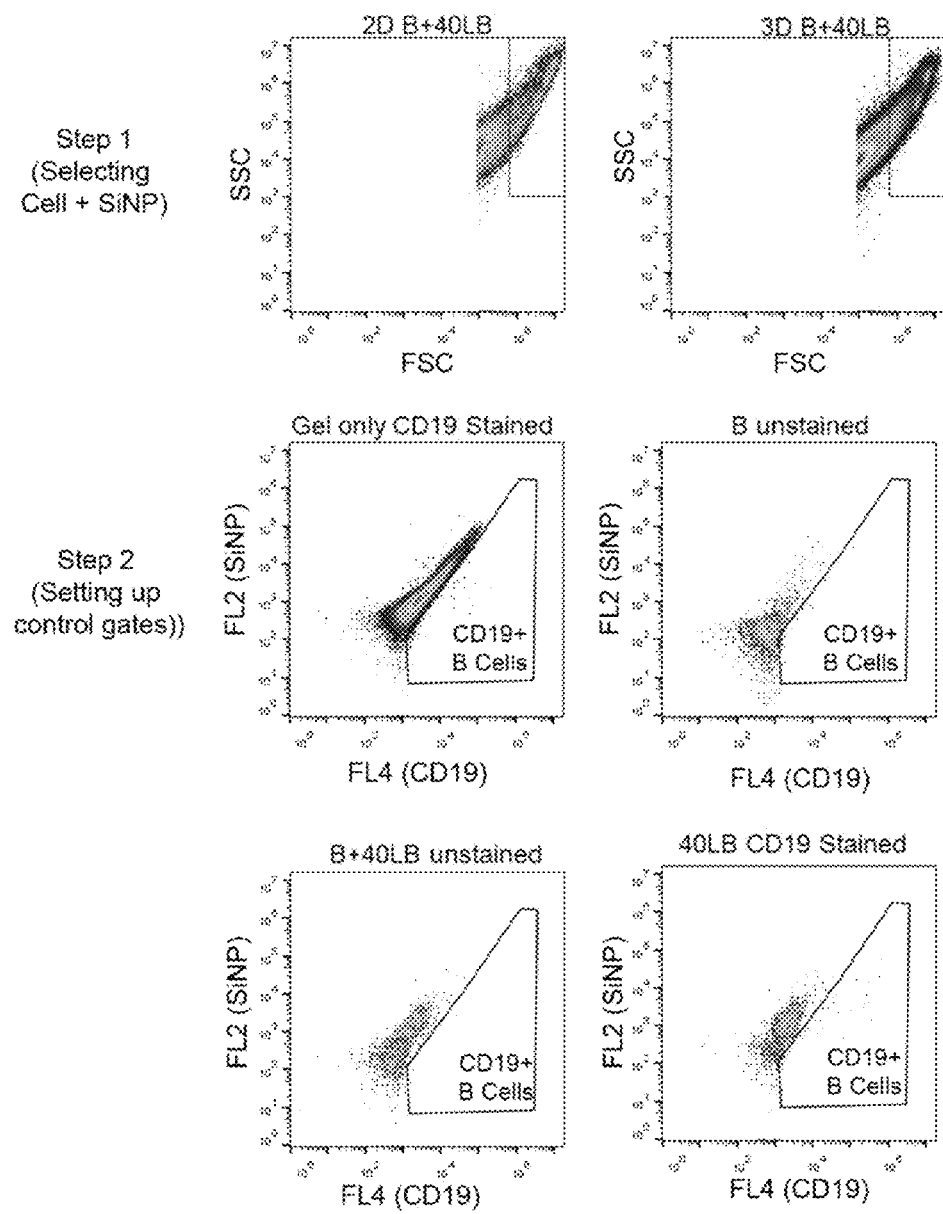
FIG. 14. Immune Organoid Flow Cytometry Gating Strategy: (1) step 1 is based on separating cell population from debris based on size via gating implemented in the FSC vs. SSC window, (2) step 2 is done to isolate CD19+ cells by preparing control gates in the FL2 vs. CD19 window with the use of unstained sample, stained stromal cells, and stained blank gel without cells encapsulated inside it, and (3) step 3 is performed for quantifying GL7+ Fas+ subset of the overall CD19+ cells by setting up control gates in the FL4 vs. FL1 window based on primary naïve B cells collected on day 0.
Figure 14:
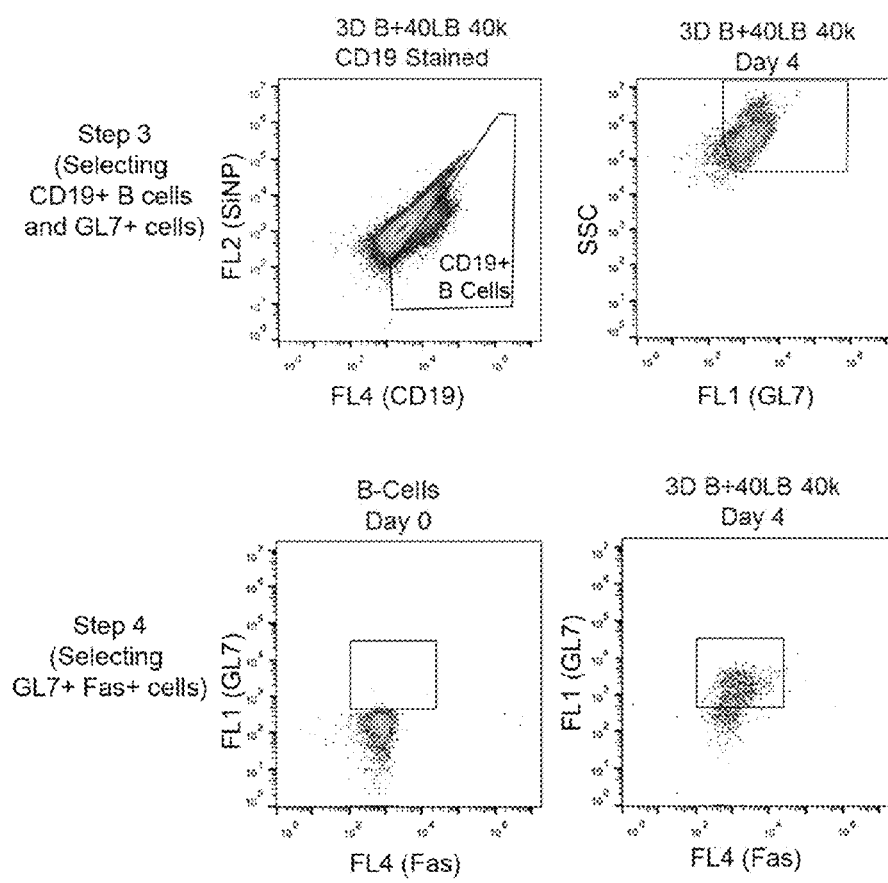

52. Add FACS buffer into the strained cell suspension and spin it down at 200 g for 5 min, at RT
53. Resuspend the cells in 100 µL of FACS buffer (note: each sample can be diluted with 200 or 300 µL of FACS buffer if the user is interested in using 2 or 3 antibody staining combinations although the diluted sample will have to be distributed into 2 or 3 100 µL suspensions)
54. Prepare antibody solution by dissolving one or more fluorophore-conjugated antibody stock solution in FACS buffer with a 1:1000 ratio or 1 µL antibody solution for every 1000 µL of FACS buffer
55. Mix 100 µL antibody solution with 100 µL cell suspension, mix gently, and incubate for 45-60 min in the dark at 4° C.
56. Spin down the stained cell suspension and aspirate the supernatant gently
57. Add 100 µL FACS buffer into each tube and store the cell suspension on ice protected from light
58. Analyze the cell suspension with flow cytometry (or use cell sorter to isolate specific cell population for biological assays)
59. Implement gating strategy based on (1) separating cell population from debris in FSC-H vs. SSC-H, (2) segmenting CD19+ cells from the rest of nanoparticles in FL2-H vs. FL4-H (or fluorescent channel of interest, and (3) analyzing the purified cell population based on the additional stains added into the sample from the perspective of absolute cell number, percentage of cell population, and/or mean fluorescent intensity. The gating scheme is summarized in FIG. 14. Antibodies are listed in Table 1.

The foregoing protocol of this Example outlines the generation of 3D immune organoid production from naïve murine B cells and their subsequent analysis. The method can be performed in a typical tissue culture room using standard equipment. Furthermore, organoids can be examined at various time points to study a variety of developmental stages. The success of preparing individual organoid droplets can vary from 90% to 100% depending on the ability to generate droplet contained in the middle of each well. In order for the organoid to demonstrate improved GC reaction kinetics, it is important to utilize serum-supplemented cell culture medium (stored at 4° C.) and add exogenous cytokines prepared fresh on the day of medium addition/replacement.

Figure 13:
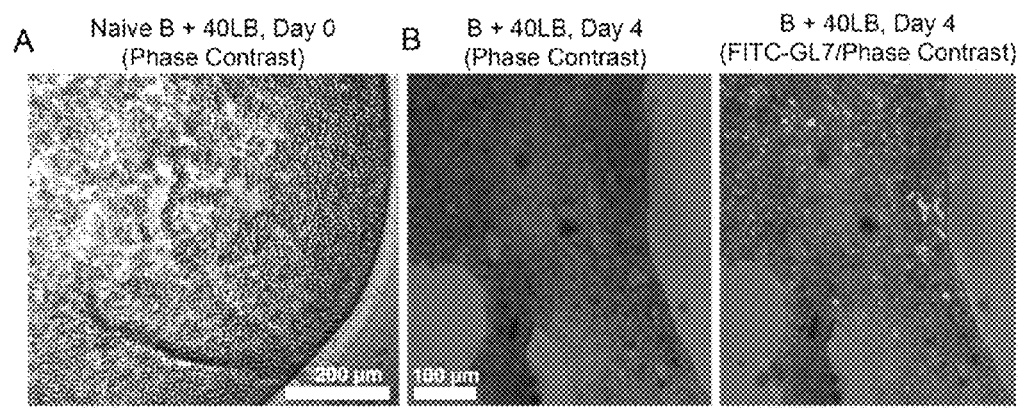
FIG. 13. Ex vivo induction into GC reaction within the immune organoid. (A) Naïve B cells with 40LB cells co-encapsulated with the immune organoids. On Day 0, freshly encapsulated cells remain spherical. (B) Immunofluorescence analysis of GC-like B cells (GL7+) in the presence of 40LB stromal cells inside the organoid.

Within 24 hr of seeding, 40LB cells will start spreading and form networks (FIG. 13A, B). We have observed that 20,000 cells/organoid formed small clusters over 48 hr whereas 40,000 and 60,000 cells/organoid resulted in dense, tightly connected cellular network. Clustering of 40LB cells can reduce the proliferation and differentiation of B cells. B cells will generally expand quickly once placed in immune organoids, and by days 4 the entire organoid will have dark spots of proliferating cells, which are difficult to examine using a standard tissue culture microscope. It is recommended to observe the organoid using a tissue culture microscope or dissecting microscope to visualize gross morphology; optimal resolution can be achieved through confocal microscopy. Differentiating B cells should be either co-localized with 40LB stromal cells or embedded in organoid matrix in close proximity to 40LBs. To obtain fine resolution images, the large size of immune organoids entails microscopic analysis by sectioning and immunohistochemical staining. After 4-6 days, organoids should begin to exhibit GC-like phenotype differentiation, marked by GL7 and Fas expression. Within the 3D organoid cultures, the CD19+GL7+ response is correlated with 40LB seeding density (FIG. 13B) where organoids with 40,000 40LB cell will induce >90-100 fold increase in CD19+GL7+ cell numbers (FIG. 14) whereas 20,000 40LB cell seeding density is expected to result in ~50-60 fold increase. 2D cultures will result in marginal 10-20 fold increase.

Another hallmark of GC reaction is the antibody class switching that occurs in GC B cells to produce antibodies with distinct effector functions. Activated B cells are known to undergo antibody class switching from IgM to IgG or other Igs. If allowed to develop further, organoids will progressively induce Ig class switching by day 6-8. Using flow cytometry on cells extracted from the organoids, one could quantitatively determine the change in surface IgM and IgG1 or another Ig subtype. Organoids can be further maintained for >10 days.

Finally, the organoid can aid in further mechanistic studies of B cell differentiation and organization, as discussed above. For example, pre-B cells stages express CD83 surface marker once they express a functional BCR. While naive B cells only express low levels of CD83, activated B cells (both in vitro and in vivo) rapidly upregulate CD83 expression levels. Yet there are several standing questions in the field of immunology and hematological malignancies because the function of CD83 during GC responses is not entirely clear. Thus, the present disclosure demonstrates that 3D immune organoids can induce a significant increase in CD83 expression in CD19+ B cells as compared to 2D co-cultures on day 4 of differentiation, which corresponds to approximately 35-fold increase over naïve B cells on day 0 (FIG. 15).

TABLE 1

| TARGET ANTIGEN | FLUOROPHORE TYPE | CLONE | SUPPLIER | CAT. NO. |
| --- | --- | --- | --- | --- |
| CD19 | PE-Cyanine7 | eBio1D3 (1D3) | eBioscience | 25-0193 |
| GL7 | Alexa Fluor 488 | GL-7 (GL7) | eBioscience | 53-5902 |
| Fas | APC | 15A7 | eBioscience | 17-0951 |
| IgM | FITC | eB121-15F9 | eBioscience | 11-5890 |
| IgG1 | APC | M1-14D12 | eBioscience | 17-4015 |

While aspects of the disclosure are illustrated by way specific embodiments, routine modifications will be apparent to those skilled in the art and such modifications are intended to be within the scope of the present disclosure.

What is claimed is:

1. An ex vivo organoid comprising B cells and stromal cells in a three dimensional material, wherein the B cells are naïve B cells, primary B cells, or a combination thereof, wherein the three dimensional material comprises a hydrogel, wherein the hydrogel is formed without exposure to ultraviolet light from an electronic ultraviolet light source, and wherein the hydrogel comprises about 1.5% silicate nanoparticles (SiNPs) that are in physical association with about 2% polyampholytic gelatin, and wherein at day 4 the organoid comprises at least 10× more CD19+ cells relative to a control organoid that does not contain about 1.5% SiNPs and about 2% polyampholytic gelatin.

2. The organoid of claim 1, wherein the physical association comprises SiNPs that are ionically bonded to the polyampholytic gelatin.

3. The organoid of claim 1, wherein the organoid is at a temperature of at least 37 degrees Celsius and the three dimensional material is not liquefied.

4. The organoid of claim 1, wherein the organoid is in contact with one or more growth factors, one or more cytokines, one or more extracellular matrix (ECM) ligands, or combinations thereof.

* * * * *